United States Patent
Watanabe et al.

(10) Patent No.: US 7,700,789 B2
(45) Date of Patent: Apr. 20, 2010

(54) HETEROGENEOUS CATALYST AND PROCESS FOR PRODUCING OXIRANE COMPOUND WITH THE CATALYST

(75) Inventors: Hisayuki Watanabe, Funabashi (JP); Kowichiro Saruhashi, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 12/292,214

(22) Filed: Nov. 13, 2008

(65) Prior Publication Data
US 2009/0082583 A1 Mar. 26, 2009

Related U.S. Application Data

(63) Continuation of application No. 10/554,546, filed as application No. PCT/JP2004/005723 on Apr. 21, 2004.

(30) Foreign Application Priority Data

| Apr. 28, 2003 | (JP) | ............................ 2003-123694 |
| Jul. 24, 2003 | (JP) | ............................ 2003-279438 |
| Feb. 20, 2004 | (JP) | ............................ 2004-044040 |

(51) Int. Cl.
C07D 301/12 (2006.01)
(52) U.S. Cl. .................................................. 549/531
(58) Field of Classification Search ................. 549/531
See application file for complete search history.

(56) References Cited

U.S. PATENT DOCUMENTS

| 4,562,276 A | 12/1985 | Venturello et al. |
| 6,063,943 A | 5/2000 | Ihm et al. |
| 6,960,693 B2 | 11/2005 | Xi et al. |

FOREIGN PATENT DOCUMENTS

| CN | A-1401425 | 3/2003 |
| JP | A 05-177143 | 7/1993 |
| JP | A 2001-523261 | 11/2001 |
| JP | A 2002-316055 | 10/2002 |

OTHER PUBLICATIONS

Venturello et al., "Quaternary Ammonium Tetrakis (diperoxotungsto) phosphates (3-) as a New Class of Catalyst for Efficient Alkene Epoxidation with Hydrogen Peroxide", J. Org. Chem. 1988, 53, 1553-1557.

Ishii et al., "Hydrogen Peroxide Oxidation Catalyzed by Heteropoly Acids Combined with Cetylpyridinium Chloride: Epoxidation of Olefins and Allylic Alcohols, Ketonization of Alcohols and Diols, and Oxidative Cleavage of 1,2-Diols and Olefins", J. Org. Chem. 1988, 53, 3587-3593.

Zuwei et al., "Reaction-Controlled Phase-Transfer Catalysis for Propylene Epoxidation to Propylene Oxide", Science, vol. 292, May 11, 2001, pp. 1139-1140.

European Search Report for European Patent Application No. 09 16 6098, Aug. 18, 2009, 7 pgs.

Ikegami, Shiro et al. "Development of a New Triphase Catalyst and Its Application to the Epoxidation of Allylic Alcohols," *Organic Letters*, 2001, pp. 1837-1840, vol. 3, No. 12.

Hoegaerts, Dirk et al. "Heterogeneous tungsten-based catalysts for the epoxidation of bulky olefins," *Catalysis Today*, 2000, pp. 209-218, vol. 60.

*Primary Examiner*—Taofiq A Solola
(74) *Attorney, Agent, or Firm*—Oliff & Berridge, PLC

(57) ABSTRACT

Process for producing an oxirane compound includes treating with hydrogen peroxide in the presence of either an olefin oxidation catalyst prepared from an organic compound or a polymer compound of formula (1)

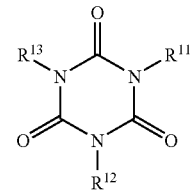

(1)

a tungstic acid compound, a phosphoric acid, hydrogen peroxide and a quaternary ammonium salt of formula (2) or (3)

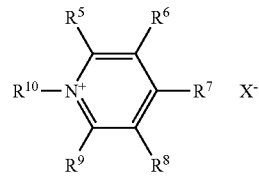

(2)

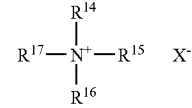

(3)

or an olefin oxidation catalyst prepared from an organic compound or a polymer compound of formula (1), a tungsten compound and a quaternary ammonium salt of formula (2) or (3). The process is useful especially industrially.

13 Claims, No Drawings

HETEROGENEOUS CATALYST AND PROCESS FOR PRODUCING OXIRANE COMPOUND WITH THE CATALYST

This is a Continuation of application Ser. No. 10/554,546 filed Oct. 27, 2005, which is a National Phase of Application No. PCT/JP2004/005723 filed Apr. 21, 2004. The disclosure of the prior applications is hereby incorporated by reference herein in their entireties.

TECHNICAL FIELD

The present invention relates to an industrial process for producing oxirane compound useful as starting material for epoxy resins used for adhesive or electronic material, or in architectural field, or the like, or for heat resistant polymers, and as an intermediate for pharmaceuticals and agrochemicals.

BACKGROUND ART

Several documents report epoxidation process with hydrogen peroxide by using as catalyst, heteropolyacid prepared separately and a quaternary ammonium salt being a phase transfer catalyst (see, for example, J. Org. Chem., Vol. 53, p. 1553-1557 (1988) and J. Org. Chem., Vol. 53, p. 3587-3595 (1988)). The epoxidation process yields only water other than the product and therefore is a very clean oxidation reaction.

However, the above-mentioned process is not necessarily a satisfactory industrial production process from reason that it uses solvents such as chloroform, dichloromethane, benzene or the like that are not used in ordinary industrial production processes, and the like. In addition, in the above-mentioned documents, although oxidation catalysts are prepared by using alkyl ammonium salt such as methyltrioctyl ammonium chloride, the oxidation catalysts have a high partition coefficient for organic solvents, and it is difficult to separate with products dissolved in organic solvents. Therefore, the process has problems in the separation and re-use of oxidation catalyst.

On the other hand, is also reported a process for making an oxidation catalyst heterogeneous by using an inorganic compound such as silica gel as a carrier (see, for example, JP 2001-17863A and JP 2001-17864 A). This process requires an expensive silane coupling agent or the like as an auxiliary substance for heterogenization, and therefore is not necessarily a satisfactory process. Industrially, further preferable oxidation catalysts are desired.

Therefore, an object of the present invention is to provide a process for producing oxirane compounds which is clean and industrially useful, and an olefin oxidation catalyst which is excellent in separability from a reaction solution and re-usability.

DISCLOSURE OF THE INVENTION

The present inventors eagerly studied in order to resolve the problems. Consequently, they found that reactions for producing oxirane with hydrogen peroxide proceed also in any solvent system normally used in industrial use by preparing an olefin oxidation catalyst from an organic compound or a polymer compound, a tungstic acid compound, phosphoric acid, hydrogen peroxide and a quaternary ammonium salt, and using the oxidation catalyst, or by preparing an olefin oxidation catalyst from an organic compound or a polymer compound, a tungsten compound and a quaternary ammonium salt, and using the oxidation catalyst, and that the oxidation catalysts exert heterogenization effect without using any auxiliary substance such as silane coupling agent or the like, and can be separated from reaction system and re-used due to a low solubility in organic solvents and water, and they completed the present invention.

That is, the present invention relates to the following aspects:

as a first aspect, an olefin oxidation catalyst, prepared from an organic compound or a polymer compound of formula (1)

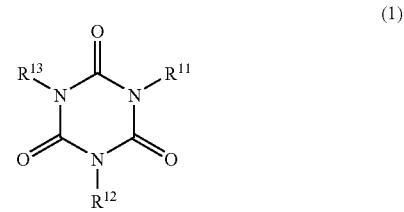

wherein $R^{11}$, $R^{12}$ and $R^{13}$ are independently of one another hydrogen atom, $C_{1-10}$alkyl group (the $C_{1-10}$alkyl group may be substituted by $C_{6-10}$aryl group), $C_{3-10}$cycloalkyl group, $C_{6-10}$aryl group, $C_{1-6}$alkylcarbonyl group (the $C_{1-6}$alkylcarbonyl group may be substituted by $C_{6-10}$aryl group) or $C_{6-10}$arylcarbonyl group;

a tungstic acid compound;

a phosphoric acid;

hydrogen peroxide; and a quaternary ammonium salt of formula (2) or (3)

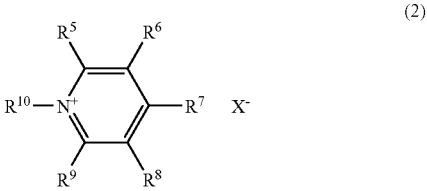

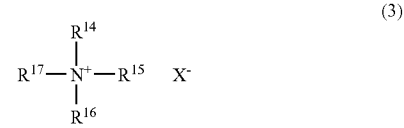

wherein $R^5$, $R^6$, $R^7$, $R^8$ and $R^9$ are independently of one another hydrogen atom, a halogen atom, cyano group, $C_{1-10}$alkyl group (the $C_{1-10}$alkyl group may be substituted by $C_{6-10}$aryl group, $C_{1-10}$alkoxy group or benzyloxy group), $C_{1-10}$alkoxy group, benzyloxy group or phenyl group, or any two of $R^5$, $R^6$, $R^7$, $R^8$ and $R^9$ together may form 1 or 2 fused benzene rings, $R^{10}$, $R^{14}$, $R^{15}$, $R^{16}$ and $R^{17}$ are independently of one another $C_{1-20}$alkyl group, and X is a halogen atom;

as a second aspect, an olefin oxidation catalyst, prepared from an organic compound or a polymer compound of formula (1)

(1)

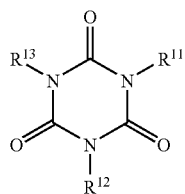

wherein $R^{11}$, $R^{12}$ and $R^{13}$ are independently of one another hydrogen atom, $C_{1-10}$alkyl group (the $C_{1-10}$alkyl group may be substituted by $C_{6-10}$aryl group), $C_{3-10}$cycloalkyl group, $C_{6-10}$aryl group, $C_{1-6}$alkylcarbonyl group (the $C_{1-6}$alkylcarbonyl group may be substituted by $C_{6-10}$aryl group) or $C_{6-10}$arylcarbonyl group;

a tungsten compound; and a quaternary ammonium salt of formula (2) or (3)

(2)

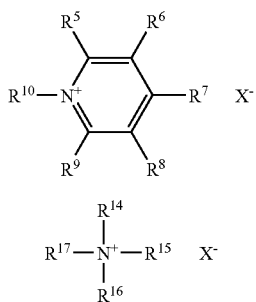

(3)

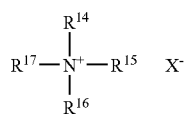

wherein $R^5$, $R^6$, $R^7$, $R^8$ and $R^9$ are independently of one another hydrogen atom, a halogen atom, cyano group, $C_{1-10}$alkyl group (the $C_{1-10}$alkyl group may be arbitrarily substituted by $C_{6-10}$aryl group, $C_{1-10}$alkoxy group or benzyloxy group), $C_{1-10}$alkoxy group, benzyloxy group or phenyl group, or any two of $R^5$, $R^6$, $R^7$, $R^8$ and $R^9$ together may form 1 or 2 fused benzene rings, $R^{10}$, $R^{14}$, $R^{15}$, $R^{16}$ and $R^{17}$ are independently of one another $C_{1-20}$alkyl group, and X is a halogen atom;

as a third aspect, the olefin oxidation catalyst as set forth in the first or second aspect, wherein the polymer compound is composed of a repeating unit of formula (8)

(8)

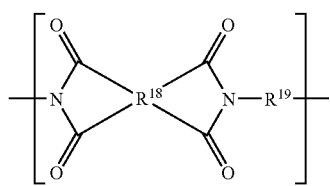

wherein $R^{18}$ is a tetravalent organic group derived from tetracarboxylic acid, and $R^{19}$ is a divalent organic group derived from diamine, and is a polyimide having a number average molecular weight of $5 \times 10^3$ or more;

as a fourth aspect, the olefin oxidation catalyst as set forth in the first, second or third aspect, wherein the quaternary ammonium salt is a compound of formula (2)

(2)

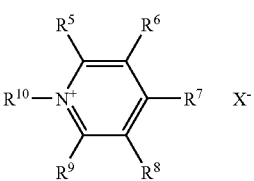

wherein $R^5$, $R^6$, $R^7$, $R^8$ and $R^9$ are independently of one another hydrogen atom, a halogen atom, cyano group, $C_{1-10}$alkyl group (the $C_{1-10}$alkyl group may be substituted by $C_{6-10}$aryl group, $C_{1-10}$alkoxy group or benzyloxy group), $C_{1-10}$alkoxy group, benzyloxy group or phenyl group, or any two of $R^5$, $R^6$, $R^7$, $R^8$ and $R^9$ together may form 1 or 2 fused benzene rings, $R^{10}$ is $C_{1-20}$alkyl group, and X is a halogen atom;

as a fifth aspect, the olefin oxidation catalyst as set forth in the fourth aspect, wherein the quaternary ammonium salt of formula (2) in which $R^5$, $R^6$, $R^7$, $R^8$ and $R^9$ are hydrogen atom is used; and as a sixth aspect, a process for producing oxirane compound of formula (5)

(5)

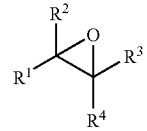

wherein $R^1$, $R^2$, $R^3$ and $R^4$ are independently of one another hydrogen atom, phenyl group, $C_{1-10}$alkyl group, $C_{3-10}$cycloalkyl group (the $C_{1-10}$alkyl group and $C_{3-10}$cycloalkyl group may be substituted by a halogen atom, phenyl group, hydroxy group or $C_{1-6}$alkoxy group), carboxyl group, $C_{1-6}$alkylcarbonyl group, $C_{1-6}$alkoxycarbonyl group (the $C_{1-6}$alkylcarbonyl group and $C_{1-6}$alkoxycarbonyl group may be substituted by a halogen atom, phenyl group, hydroxy group or $C_{1-6}$alkoxy group) or phenoxycarbonyl group (the phenoxycarbonyl group may be substituted by a halogen atom, phenyl group, $C_{1-6}$alkyl group or $C_{1-6}$alkoxy group), or any two of $R^1$, $R^2$, $R^3$ and $R^4$ together are —$(CH_2)_m$— wherein m is 3, 4 or 5, —$CO_2(CH_2)_n$— wherein n is 1, 2 or 3, —$CO(CH_2)_o$— wherein o is 2, 3 or 4, —$(CH_2)_p$—O—$(CH_2)_q$— wherein p and q are independently of each other 0, 1, 2, 3 or 4, and a sum of p and q is 2, 3 or 4,

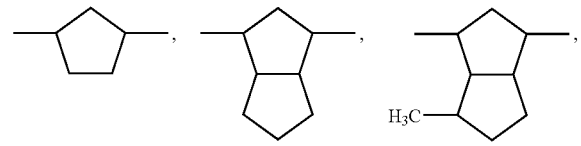

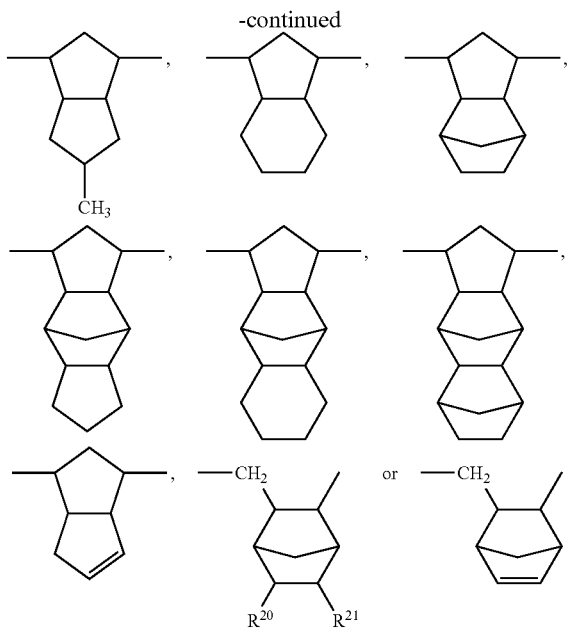

wherein $R^{20}$ and $R^{21}$ are independently of one another hydrogen atom or $C_{1-6}$alkoxy group (the $C_{1-6}$alkoxy group may be substituted by $C_{2-4}$alkenyl group or phenyl group (the phenyl group may be substituted by a halogen atom, $C_{1-6}$alkyl group or $C_{1-10}$alkoxy group)), characterized by treating an olefin of formula (4)

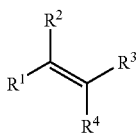 (4)

wherein $R^1$, $R^2$, $R^3$ and $R^4$ have the same meaning as the above, with hydrogen peroxide in the presence of the olefin oxidation catalyst as set forth in the first, second, third, fourth or fifth aspect.

BEST MODE FOR CARRYING OUT THE INVENTION

Hereinafter, the present invention will be described in further detail.

In the meanwhile, in the present specification, "n" means normal, "i" means iso, "s" means secondary, "t" means tertiary, and "c" means cyclo.

First of all, the definition of each substituent of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and X will be described.

$C_{1-6}$alkyl group includes methyl group, ethyl group, n-propyl group, i-propyl group, n-butyl group, i-butyl group, s-butyl group, t-butyl group, n-pentyl group, 1-methyl-n-butyl group, 2-methyl-n-butyl group, 3-methyl-n-butyl group, 1,1-dimethyl-n-propyl group, 1,2-dimethyl-n-propyl group, 2,2-dimethyl-n-propyl group, 1-ethyl-n-propyl group, n-hexyl group, 1-methyl-n-pentyl group, 2-methyl-n-pentyl group, 3-methyl-n-pentyl group, 4-methyl-n-pentyl group, 1,1-dimethyl-n-butyl group, 1,2-dimethyl-n-butyl group, 1,3-dimethyl-n-butyl group, 2,2-dimethyl-n-butyl group, 2,3-dimethyl-n-butyl group, 3,3-dimethyl-n-butyl group, 1-ethyl-n-butyl group, 2-ethyl-n-butyl group, 1,1,2-trimethyl-n-propyl group, 1,2,2-trimethyl-n-propyl group, 1-ethyl-1-methyl-n-propyl group, 1-ethyl-2-methyl-n-propyl group, etc.

$C_{1-10}$ alkyl group includes in addition to the above, 1-methyl-1-ethyl-n-pentyl group, 1-heptyl group, 2-heptyl group, 1-ethyl-1,2-dimethyl-n-propyl group, 1-ethyl-2,2-dimethyl-n-propyl group, 1-octyl group, 3-octyl group, 4-methyl-3-n-heptyl group, 6-methyl-2-n-heptyl group, 2-propyl-1-n-heptyl group, 2,4,4-trimethyl-1-n-pentyl group, 1-nonyl group, 2-nonyl group, 2,6-dimethyl-4-n-heptyl group, 3-ethyl-2,2-dimethyl-3-n-pentyl group, 3,5,5-trimethyl-1-n-hexyl group, 1-decyl group, 2-decyl group, 4-decyl group, 3,7-dimethyl-1-n-octyl group, 3,7-dimethyl-3-n-octyl group, etc.

$C_{1-20}$alkyl group includes in addition to the above, n-undecyl group, n-dodecyl group, n-tridecyl group, n-tetradecyl group, n-pentadecyl group, n-hexadecyl group, n-heptadecyl group, n-octadecyl group, n-nonadecyl group, n-eicosyl, etc.

$C_{3-10}$cycloalkyl group includes c-propyl group, c-butyl group, 1-methyl-c-propyl group, 2-methyl-c-propyl group, c-pentyl group, 1-methyl-c-butyl group, 2-methyl-c-butyl group, 3-methyl-c-butyl group, 1,2-dimethyl-c-propyl group, 2,3-dimethyl-c-propyl group, 1-ethyl-c-propyl group, 2-ethyl-c-propyl group, c-hexyl group, 1-methyl-c-pentyl group, 2-methyl-c-pentyl group, 3-methyl-c-pentyl group, 1-ethyl-c-butyl group, 2-ethyl-c-butyl group, 3-ethyl-c-butyl group, 1,2-dimethyl-c-butyl group, 1,3-dimethyl-c-butyl group, 2,2-dimethyl-c-butyl group, 2,3-dimethyl-c-butyl group, 2,4-dimethyl-c-butyl group, 3,3-dimethyl-c-butyl group, 1-n-propyl-c-propyl group, 2-n-propyl-c-propyl group, 1-i-propyl-c-propyl group, 2-i-propyl-c-propyl group, 1,2,2-trimethyl-c-propyl group, 1,2,3-trimethyl-c-propyl group, 2,2,3-trimethyl-c-propyl group, 1-ethyl-2-methyl-c-propyl group, 2-ethyl-1-methyl-c-propyl group, 2-ethyl-2-methyl-c-propyl group, 2-ethyl-3-methyl-c-propyl group, c-heptyl group, c-octyl group, c-nonyl group, c-decyl group, etc.

$C_{6-10}$arylcarbonyl group includes benzoyl group, 1-indenylcarbonyl group, 2-indenylcarbonyl group, 3-indenylcarbonyl group, 4-indenylcarbonyl group, 5-indenylcarbonyl group, 6-indenylcarbonyl group, 7-indenylcarbonyl group, 1-naphthoyl group, 2-naphthoyl group, 1-tetrahydronaphthoyl group, 2-tetrahydronaphthoyl group, 5-tetrahydronaphthoyl group, 6-tetrahydronaphthoyl group, etc.

$C_{1-6}$alkoxy group includes methoxy group, ethoxy group, n-propoxy group, i-propoxy group, n-butoxy group, i-butoxy group, s-butoxy group, t-butoxy group, n-pentyloxy group, 1-methyl-n-butoxy group, 2-methyl-n-butoxy group, 3-methyl-n-butoxy group, 1,1-dimethyl-n-propoxy group, 1,2-dimethyl-n-propoxy group, 2,2-dimethyl-n-propoxy group, 1-ethyl-n-propoxy group, 1-hexyloxy group, 1-methyl-n-pentyloxy group, 2-methyl-n-pentyloxy group, 3-methyl-n-pentyloxy group, 4-methyl-n-pentyloxy group, 1,1-dimethyl-n-butoxy group, 1,2-dimethyl-n-butoxy group, 1,3-dimethyl-n-butoxy group, 2,2-dimethyl-n-butoxy group, 2,3-dimethyl-n-butoxy group, 3,3-dimethyl-n-butoxy group, 1-ethyl-n-butoxy group, 2-ethyl-n-butoxy group, 1,1,2-trimethyl-n-propoxy group, 1,2,2-trimethyl-n-propoxy group, 1-ethyl-1-methyl-n-propoxy group, 1-ethyl-2-methyl-n-propoxy group, etc.

$C_{1-10}$alkoxy group includes in addition to the above, 1-methyl-1-ethyl-n-pentyloxy group, 1-heptyloxy group, 2-heptyloxy group, 1-ethyl-1,2-dimethyl-n-propoxy group, 1-ethyl-2,2-dimethyl-n-propoxy group, 1-octyloxy group, 3-octyloxy group, 4-methyl-3-n-heptyloxy group, 6-methyl-2-n-heptyloxy group, 2-propyl-1-n-heptyloxy group, 2,4,4- trimethyl-1-n-pentyloxy group, 1-nonyloxy group, 2-nonyloxy group, 2,6-dimethyl-4-n-heptyloxy group, 3-ethyl-2,2-dimethyl-3-n-pentyloxy group, 3,5,5-trimethyl-1-n-hexyloxy group, 1-decyloxy group, 2-decyloxy group, 4-decyloxy group, 3,7-dimethyl-1-n-octyloxy group, 3,7-dimethyl-3-n-octyloxy group, etc.

$C_{1-6}$alkylcarbonyl group includes methylcarbonyl group, ethylcarbonyl group, n-propylcarbonyl group, i-propylcarbonyl group, n-butylcarbonyl group, i-butylcarbonyl group, s-butylcarbonyl group, t-butylcarbonyl group, n-pentylcarbonyl group, 1-methyl-n-butylcarbonyl group, 2-methyl-n-butylcarbonyl group, 3-methyl-n-butylcarbonyl group, 1,1-dimethyl-n-propylcarbonyl group, 1,2-dimethyl-n-propylcarbonyl group, 2,2-dimethyl-n-propylcarbonyl group, 1-ethyl-n-propylcarbonyl group, n-hexylcarbonyl group, 1-methyl-n-pentylcarbonyl group, 2-methyl-n-pentylcarbonyl, 3-methyl-n-pentylcarbonyl, 4-methyl-n-pentylcarbonyl, 1,1-dimethyl-n-butylcarbonyl group, 1,2-dimethyl-n-butylcarbonyl group, 1,3-dimethyl-n-butylcarbonyl group, 2,2-dimethyl-n-butylcarbonyl group, 2,3-dimethyl-n-butylcarbonyl group, 3,3-dimethyl-n-butylcarbonyl group, 1-ethyl-n-butylcarbonyl group, 2-ethyl-n-butylcarbonyl group, 1,1,2-trimethyl-n-propylcarbonyl group, 1,2,2-trimethyl-n-propylcarbonyl group, 1-ethyl-1-methyl-n-propylcarbonyl group, 1-ethyl-2-methyl-n-propylcarbonyl group, etc.

$C_{1-6}$alkoxycarbonyl group includes methoxycarbonyl group, ethoxycarbonyl group, n-propoxycarbonyl group, i-propoxycarbonyl group, n-butoxycarbonyl group, i-butoxycarbonyl group, s-butoxycarbonyl group, t-butoxycarbonyl group, n-pentyloxycarbonyl group, 1-methyl-n-butoxycarbonyl group, 2-methyl-n-butoxycarbonyl group, 3-methyl-n-butoxycarbonyl group, 1,1-dimethyl-n-propoxycarbonyl group, 1,2-dimethyl-n-propoxycarbonyl group, 2,2-dimethyl-n-propoxycarbonyl group, 1-ethyl-n-propoxycarbonyl group, n-hexyloxycarbonyl group, 1-methyl-n-pentyloxycarbonyl group, 2-methyl-n-pentyloxycarbonyl, 3-methyl-n-pentyloxycarbonyl, 4-methyl-n-pentyloxycarbonyl, 1,1-dimethyl-n-butoxycarbonyl group, 1,2-dimethyl-n-butoxycarbonyl group, 1,3-dimethyl-n-butoxycarbonyl group, 2,2-dimethyl-n-butoxycarbonyl group, 2,3-dimethyl-n-butoxycarbonyl group, 3,3-dimethyl-n-butoxycarbonyl group, 1-ethyl-n-butoxycarbonyl group, 2-ethyl-n-butoxycarbonyl group, 1,1,2-trimethyl-n-propoxycarbonyl group, 1,2,2-trimethyl-n-propoxycarbonyl group, 1-ethyl-1-methyl-n-propoxycarbonyl group, 1-ethyl-2-methyl-n-propoxycarbonyl group, etc.

$C_{6-10}$aryl group includes phenyl group, 1-indenyl group, 2-indenyl group, 3-indenyl group, 4-indenyl group, 5-indenyl group, 6-indenyl group, 7-indenyl group, 1-naphthyl group, 2-naphthyl group, 1-tetrahydronaphthyl group, 2-tetrahydronaphthyl group, 5-tetrahydronaphthyl group, 6-tetrahydronaphthyl group, etc.

$C_{2-4}$ alkenyl group includes ethenyl group, 1-propenyl group, 2-propenyl group, 1-butenyl group, 2-butenyl group, 3-butenyl group, 2-methyl-1-propenyl group, 2-methyl-2-propenyl group, 1-methyl-1-propenyl group, 1-methyl-2-propenyl group, 1-ethyl-1-ethenyl group, etc.

Halogen atom includes fluorine atom, chlorine atom, bromine atom and iodine atom.

Then, specific examples of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and X will be described.

Specific examples of $R^1$, $R^2$, $R^3$ and $R^4$ include hydrogen atom, methyl group, ethyl group, n-propyl group, i-propyl group, n-butyl group, i-butyl group, s-butyl group, t-butyl group, n-pentyl group, n-hexyl group, n-heptyl group, n-octyl group, n-nonyl group, n-decyl group, c-hexyl group, phenyl group, chloromethyl group, bromomethyl group, hydroxymethyl group, methoxymethyl group, ethoxymethyl group, phenoxymethyl group, carboxyl group, methylcarbonyl group, ethylcarbonyl group, n-propylcarbonyl group, n-butylcarbonyl group, n-pentylcarbonyl group, n-hexylcarbonyl group, methoxycarbonyl group, ethoxycarbonyl group, n-propoxycarbonyl group, n-butoxycarbonyl group, n-pentyloxycarbonyl group, n-hexyloxycarbonyl group, phenoxycarbonyl group, etc.

Specific examples of groups that any two of $R^1$, $R^2$, $R^3$ and $R^4$ form together include groups of the following formulae

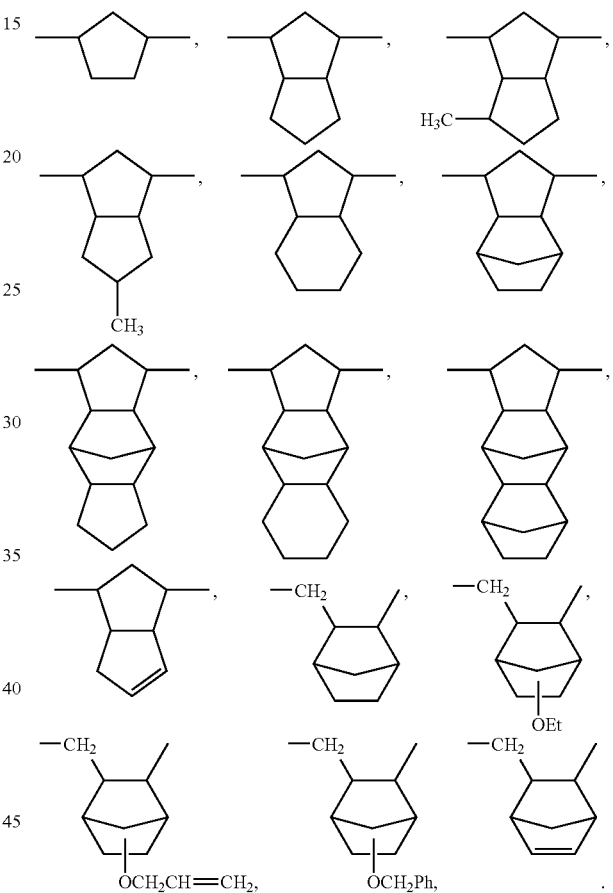

Specific examples of $R^5$, $R^6$, $R^7$, $R^8$ and $R^9$ include hydrogen atom, fluorine atom, chlorine atom, bromine atom, iodine atom, cyano group, methyl group, ethyl group, n-propyl group, i-propyl group, n-butyl group, i-butyl group, s-butyl group, t-butyl group, n-pentyl group, n-hexyl group, n-heptyl group, n-octyl group, n-nonyl group, n-decyl group, methoxy group, ethoxy group, n-propyloxy group, i-propyloxy group, n-butoxy group, i-butoxy group, s-butoxy group, t-butoxy group, n-pentyloxy group, n-hexyloxy group, n-heptyloxy group, n-octyloxy group, n-nonyloxy group, n-decyloxy group, benzyloxy group, benzyl group, 3-phenylpropyl group, etc., and hydrogen atom is preferable.

Specific examples of fused benzene ring that any two of $R^5$, $R^6$, $R^7$, $R^8$ and $R^9$ form together include a case where $R^5$ and $R^6$ together form —CH=CH—CH=CH—, a case where $R^6$ and $R^7$ together form —CH=CH—CH=CH—, and a case where $R^5$ and $R^6$ together form —CH=CH—CH=CH— and $R^8$ and $R^9$ together form —CH=CH—CH=CH—.

Specific examples of $R^{10}$ include $CH_3$—, $H(CH_2)_2$—, $H(CH_2)_3$—, $H(CH_2)_4$—, $H(CH_2)_5$—, $H(CH_2)_6$—, $H(CH_2)_7$—, $H(CH_2)_8$—, $H(CH_2)_9$—, $H(CH_2)_{10}$—, $H(CH_2)_{11}$—, $H(CH_2)_{12}$—, $H(CH_2)_{13}$—, $H(CH_2)_{14}$—, $H(CH_2)_{15}$—, $H(CH_2)_{16}$—, $H(CH_2)_{17}$—, $H(CH_2)_{18}$—, $H(CH_2)_{19}$— and $H(CH_2)_{20}$—, etc., and $H(CH_2)_{14}$—, $H(CH_2)_{16}$—, $H(CH_2)_{18}$— and $H(CH_2)_{20}$— are preferable.

Specific examples of $R^{11}$, $R^{12}$ and $R^{13}$ include hydrogen atom, methyl group, ethyl group, n-propyl group, i-propyl group, n-butyl group, i-butyl group, s-butyl group, t-butyl group, n-pentyl group, 1-methyl-n-butyl group, 2-methyl-n-butyl group, 3-methyl-n-butyl group, 1,1-dimethyl-n-propyl group, 1,2-dimethyl-n-propyl group, 2,2-dimethyl-n-propyl group, 1-ethyl-n-propyl group, n-hexyl group, 1-methyl-n-pentyl group, 2-methyl-n-pentyl group, 3-methyl-n-pentyl group, 4-methyl-n-pentyl group, 1,1-dimethyl-n-butyl group, 1,2-dimethyl-n-butyl group, 1,3-dimethyl-n-butyl group, 2,2-dimethyl-n-butyl group, 2,3-dimethyl-n-butyl group, 3,3-dimethyl-n-butyl group, 1-ethyl-n-butyl group, 2-ethyl-n-butyl group, 1,1,2-trimethyl-n-propyl group, 1,2,2-trimethyl-n-propyl group, 1-ethyl-1-methyl-n-propyl group, 1-ethyl-2-methyl-n-propyl group, 1-methyl-1-ethyl-n-pentyl group, n-heptyl group, 2-heptyl group, 1-ethyl-1,2-dimethyl-n-propyl group, 1-ethyl-2,2-dimethyl-n-propyl group, 1-octyl group, 3-octyl group, 4-methyl-3-n-heptyl group, 6-methyl-2-n-heptyl group, 2-propyl-1-n-heptyl group, 2,4,4-trimethyl-1-n-pentyl group, 1-nonyl group, 2-nonyl group, 2,6-dimethyl-4-n-heptyl group, 3-ethyl-2,2-dimethyl-3-n-pentyl group, 3,5,5-trimethyl-1-n-hexyl group, 1-decyl group, 2-decyl group, 4-decyl group, 3,7-dimethyl-1-n-octyl group, 3,7-dimethyl-3-n-octyl group, c-propyl group, c-butyl group, 1-methyl-c-propyl group, 2-methyl-c-propyl group, c-pentyl group, 1-methyl-c-butyl group, 2-methyl-c-butyl group, 3-methyl-c-butyl group, 1,2-dimethyl-c-propyl group, 2,3-dimethyl-c-propyl group, 1-ethyl-c-propyl group, 2-ethyl-c-propyl group, c-hexyl group, 1-methyl-c-pentyl group, 2-methyl-c-pentyl group, 3-methyl-c-pentyl group, 1-ethyl-c-butyl group, 2-ethyl-c-butyl group, 3-ethyl-c-butyl group, 1,2-dimethyl-c-butyl group, 1,3-dimethyl-c-butyl group, 2,2-dimethyl-c-butyl group, 2,3-dimethyl-c-butyl group, 2,4-dimethyl-c-butyl group, 3,3-dimethyl-c-butyl group, 1-n-propyl-c-propyl group, 2-n-propyl-c-propyl group, 1-i-propyl-c-propyl group, 2-i-propyl-c-propyl group, 1,2,2-trimethyl-c-propyl group, 1,2,3-trimethyl-c-propyl group, 2,2,3-trimethyl-c-propyl group, 1-ethyl-2-methyl-c-propyl group, 2-ethyl-1-methyl-c-propyl group, 2-ethyl-2-methyl-c-propyl group, 2-ethyl-3-methyl-c-propyl group, c-heptyl group, c-octyl group, c-nonyl group, c-decyl group, benzyl group, phenyl group, methylcarbonyl group, ethylcarbonyl group, n-propylcarbonyl group, i-propylcarbonyl group, n-butylcarbonyl group, benzoyl group, 1-naphthoyl group, 2-naphthoyl group, etc., and hydrogen atom, methyl group, ethyl group, n-propyl group, i-propyl group, n-butyl group, i-butyl group and phenyl group are preferable.

Specific examples of $R^{14}$, $R^{15}$, $R^{16}$ and $R^{17}$ include benzyl group, $CH_3$—, $H(CH_2)_2$—, $H(CH_2)_3$—, $H(CH_2)_4$—, $H(CH_2)_5$—, $H(CH_2)_6$—, $H(CH_2)_7$—, $H(CH_2)_8$—, $H(CH_2)_9$—, $H(CH_2)_{10}$—, $H(CH_2)_{11}$—, $H(CH_2)_{12}$—, $H(CH_2)_{13}$—, $H(CH_2)_{14}$—, $H(CH_2)_{15}$—, $H(CH_2)_{16}$—, $H(CH_2)_{17}$—, $H(CH_2)_{18}$—, $H(CH_2)_{19}$— and $H(CH_2)_{20}$—, etc., and benzyl group, $CH_3$—, $H(CH_2)_2$—, $H(CH_2)_8$—, $H(CH_2)_{14}$—, $H(CH_2)_{16}$—, $H(CH_2)_{18}$— and $H(CH_2)_{20}$— are preferable.

Specific examples of tetracarboxylic acid forming $R^{18}$ include aromatic tetracarboxylic acids such as pyromellitic acid, 2,3,6,7-naphthalenetetracarboxylic acid, 1,2,5,6-naphthalenetetracarboxylic acid, 1,4,5,8-naphthalenetetracarboxylic acid, 2,3,6,7-anthracenetetracarboxylic acid, 1,2,5,6-anthracenetetracarboxylic acid, 3,3',4,4'-biphenyltetracarboxylic acid, 2,3,3',4-biphenyltetracarboxylic acid, bis(3,4-dicarboxyphenyl) ether, 3,3',4,4'-benzophenone tetracarboxylic acid, bis(3,4-dicarboxyphenyl)sulfone, bis(3,4-dicarboxyphenyl) methane, 2,2-bis(3,4-dicarboxyphenyl) propane, 1,1,1,3,3,3-hexafluoro-2,2-bis(3,4-dicarboxyphenyl) propane, bis(3,4-dicarboxyphenyl) dimethylsilane, bis(3,4-dicarboxyphenyl) diphenylsilane, 2,3,4,5-pyridinetetracarboxylic acid, 2,6-bis(3,4-dicarboxyphenyl)pyridine, etc.; alicyclic tetracarboxylic acids such as 1,2,3,4-cyclobutane tetracarboxylic acid, 1,2,3,4-cycloheptane tetracarboxylic acid, 2,3,4,5-tetrahydrofuran tetracarboxylic acid, 1,2,4,5-cyclohexane tetracarboxylic acid, 5-succinic acid-3-methyl-cyclohexene-1,2-dicarboxylic acid, 3,4-dicarboxy-1,2,3,4-tetrahydronaphthalene-1-succinic acid, etc.; aliphatic tetracarboxylic acids such as 1,2,3,4-butane tetracarboxylic acid, 1,2,3,4-cyclobutane tetracarboxylic acid, 2,3,5-tricarboxy-2-cyclopentane acetic acid, 3,5,6-tricarboxy-2-norbornane acetic acid, etc., and these compounds can be used in a mixture of two or more. Preferable tetracarboxylic acids are 3,3',4,4'-biphenyltetracarboxylic acid, 3,3',4,4'-biphenyltetracarboxylic acid, 1,1,1,3,3,3-hexafluoro-2,2-bis(3,4-dicarboxyphenyl) propane, 1,2,3,4-cyclobutane tetracarboxylic acid, 1,2,3,4-cyclopentane tetracarboxylic acid, 1,2,4,5-cyclohexane tetracarboxylic acid, 5-succinic acid-3-methyl-3-cyclohexene-1,2-dicarboxylic acid, 3,4-dicarboxy-1,2,3,4-tetrahydronaphthalene-1-succinic acid, 1,2,3,4-butane tetracarboxylic acid, 1,2,3,4-cyclobutane tetracarboxylic acid, etc.

Specific examples of diamine forming $R^{19}$ include aromatic diamines such as p-phenylenediamine, m-phenylenediamine, 2,5-diaminotoluene, 2,6-diaminotoluene, 4,4'-diaminobiphenyl, 3,3'-dimethyl-4,4'-diaminobiphenyl, 3,3'-dimethoxy-4,4'-diaminobiphenyl, 3,3'-diethyl-4,4'-diaminobiphenyl, 4,4'-diaminodiphenylmethane, 4,4'-diaminodiphenyl ether, 4,4'-isopropylidene bisaniline, bis(3,5-diethyl-4-aminophenyl)methane, 4,4'-diaminodiphenylsulfone, 4,4'-diaminobenzophenone, 1,4-diaminonaphthalene, 1,5-diaminonaphthalene, 1,4-bis(4-aminophenoxy)benzene, 1,4-bis(4-aminophenyl)benzene, 9,10-bis(4-aminophenyl) anthracene, 1,3-bis(4-aminophenoxy)benzene, bis[4-(4-aminophenoxy)phenyl] sulfone, 4,4'-bis(4-aminophenoxy) diphenylsulfone, 2,2-bis[4-(4-aminophenoxy)phenyl] propane, 2,2-bis(4-aminophenoxy) hexafluoropropane, 2,2-bis[4-(4-aminophenoxy)phenyl] hexafluoropropane, etc.; alicyclic diamines such as bis(4-aminocyclohexyl)methane, bis(4-amino-3-methylcyclohexyl)methane, etc.; and aliphatic diamines such as 1,2-diaminoethane, 1,3-diaminopropane, 1,4-diaminobutane, 1,6-diaminohexane, etc., and these compounds can be used in a mixture of two or more. Preferable diamines are p-phenylenediamine, m-phenylenediamine, 3,3'-dimethyl-4,4'-diaminobiphenyl, 3,3'-diethyl-4,4'-diaminobiphenyl, 4,4'-diaminodiphenylmethane, 4,4'-diaminodiphenyl ether, bis(3,5-diethyl-4-aminophenyl)methane, 4,4'-diaminodiphenylsulfone, 1,5-diaminonaphthalene, 1,4-bis(4-aminophenoxy)benzene, 1,3-bis(4-aminophenoxy)benzene, bis(4-aminocyclohexyl)methane, bis(4-amino-3-methylcyclohexyl)methane, 1,2-diaminoethane, 1,3-diaminopropane, 1,4-diaminobutane, 1,6-diaminohexane, etc.

Specific examples of X include fluorine atom, chlorine atom, bromine atom and iodine atom, and chlorine atom is preferable.

Preferable organic compounds are compounds of formula (1) wherein any two of $R^{11}$, $R^{12}$ and $R^{13}$ are hydrogen atom, the remaining one is methyl group, ethyl group, n-propyl group, i-propyl group, n-butyl, i-butyl group, phenyl group, etc.

Preferable quaternary ammonium salts of formula (2) include the following compounds:

1) quaternary ammonium salts of formula (2) wherein $R^{10}$ is $H(CH_2)_{14}$—, $H(CH_2)_{16}$—, $H(CH_2)_{18}$— or $H(CH_2)_{20}$—;

2) quaternary ammonium salts of formula (2) wherein $R^5$, $R^6$, $R^7$, $R^8$ and $R^9$ are hydrogen atom;

3) quaternary ammonium salts of formula (2) wherein $R^{10}$ is $H(CH_2)_{14}$—, $H(CH_2)_{16}$—, $H(CH_2)_{18}$— or $H(CH_2)_{20}$—, and $R^5$, $R^6$, $R^7$, $R^8$ and $R^9$ are hydrogen atom.

Preferable quaternary ammonium salts of formula (3) include commercially available trioctylmethyl ammonium salts, benzylcetyldimethyl ammonium salts, benzyldimethylstearyl ammonium salts, cetyldimethylethyl ammonium salts, dimethyldistearyl ammonium salts, stearyltrimethyl ammonium salts, etc.

Polyimides composed of a repeating unit of formula (8) are specifically limited so far as they can heterogenize an olefin oxidation catalyst prepared from a tungstic acid compound, a phosphoric acid, hydrogen peroxide and a quaternary ammonium, or an olefin oxidation catalyst prepared from a tungsten compound and a quaternary ammonium salt, but they generally have a lower limit of number average molecular weight of $5\times10^3$, preferably $8\times10^3$, and an upper limit of $2\times10^5$, for example $1\times10^5$, or preferably for example $3\times10^4$.

Preferable combination of tetracarboxylic acid forming $R^{18}$ with diamine forming $R^{19}$ is as follows:

1) polyimides composed of repeating unit of formula (8) in which the tetracarboxylic acid forming $R^{18}$ is pyromellitic acid, 2,3,6,7-naphthalenetetracarboxylic acid, 1,2,5,6-naphthalenetetracarboxylic acid, 1,4,5,8-naphthalenetetracarboxylic acid, 2,3,6,7-anthracenetetracarboxylic acid, 1,2,5,6-anthracenetetracarboxylic acid, 3,3',4,4'-biphenyltetracarboxylic acid, 2,3,3',4'-biphenyltetracarboxylic acid, bis(3,4-dicarboxyphenyl) ether, 3,3',4,4'-benzophenone tetracarboxylic acid, bis(3,4-dicarboxyphenyl) sulfone, bis(3,4-dicarboxyphenyl) methane, 2,2-bis(3,4-dicarboxyphenyl) propane, 1,1,1,3,3,3-hexafluoro-2,2-bis(3,4-dicarboxyphenyl) propane, bis(3,4-dicarboxyphenyl) dimethylsilane, bis(3,4-dicarboxyphenyl) diphenylsilane, 2,3,4,5-pyridinetetracarboxylic acid, 2,6-bis(3,4-dicarboxyphenyl)pyridine, 1,2,3,4-cyclobutane tetracarboxylic acid, 1,2,3,4-cycloheptane tetracarboxylic acid, 2,3,4,5-tetrahydrofuran tetracarboxylic acid, 1,2,4,5-cyclohexane tetracarboxylic acid, 5-succinic acid-3-methyl-cyclohexene-1,2-dicarboxylic acid, 3,4-dicarboxy-1,2,3,4-tetrahydronaphthalene-1-succinic acid, 1,2,3,4-butane tetracarboxylic acid, 1,2,3,4-cyclobutane tetracarboxylic acid, 2,3,5-tricarboxy-2-cyclopentane acetic acid or 3,5,6-tricarboxy-2-norbornane acetic acid, or a mixture of two or more of these, and the diamine forming $R^{19}$ is p-phenylenediamine, m-phenylenediamine, 3,3'-dimethyl-4,4'-diaminobiphenyl, 3,3'-diethyl-4,4'-diaminobiphenyl, 4,4'-diaminodiphenylmethane, 4,4'-diaminodiphenyl ether, bis(3,5-diethyl-4-aminophenyl)methane, 4,4'-diaminodiphenylsulfone, 1,5-diaminonaphthalene, 1,4-bis(4-aminophenoxy)benzene, 1,3-bis(4-aminophenoxy)benzene, bis(4-aminocyclohexyl)methane, bis(4-amino-3-methylcyclohexyl)methane, 1,2-diaminoethane, 1,3-diaminopropane, 1,4-diaminobutane or 1,6-diaminohexane;

2) polyimides composed of repeating unit of formula (8) in which the tetracarboxylic acid forming $R^{18}$ is 3,3',4,4'-biphenyltetracarboxylic acid, 3,3',4,4'-biphenyltetracarboxylic acid, 1,1,1,3,3,3-hexafluoro-2,2-bis(3,4-dicarboxyphenyl) propane, 1,2,3,4-cyclobutane tetracarboxylic acid, 1,2,3,4-cyclopentane tetracarboxylic acid, 1,2,4,5-cyclohexane tetracarboxylic acid, 5-succinic acid-3-methyl-3-cyclohexene-1,2-dicarboxylic acid, 3,4-dicarboxy-1,2,3,4-tetrahydronaphthalene-1-succinic acid, 1,2,3,4-butane tetracarboxylic acid or 1,2,3,4-cyclobutane tetracarboxylic acid, and the diamine forming $R^{19}$ is p-phenylenediamine, m-phenylenediamine, 2,5-diaminotoluene, 2,6-diaminotoluene, 4,4'-diaminobiphenyl, 3,3'-dimethyl-4,4'-diaminobiphenyl, 3,3'-dimethoxy-4,4'-diaminobiphenyl, 3,3'-diethyl-4,4'-diaminobiphenyl, 4,4'-diaminodiphenylmethane, 4,4'-diaminodiphenyl ether, 4,4'-isopropylidene bisaniline, bis(3,5-diethyl-4-aminophenyl)methane, 4,4'-diaminodiphenylsulfone, 4,4'-diaminobenzophenone, 1,4-diaminonaphthalene, 1,5-diaminonaphthalene, 1,4-bis(4-aminophenoxy)benzene, 1,4-bis(4-aminophenyl)benzene, 9,10-bis(4-aminophenyl) anthracene, 1,3-bis(4-aminophenoxy)benzene, bis[4-(4-aminophenoxy)phenyl] sulfone, 4,4'-bis(4-aminophenoxy) diphenylsulfone, 2,2-bis[4-(4-aminophenoxy)phenyl] propane, 2,2-bis(4-aminophenyl) hexafluoropropane, 2,2-bis[4-(4-aminophenoxy)phenyl] hexafluoropropane, bis(4-aminocyclohexyl)methane, bis(4-amino-3-methylcyclohexyl)methane, 1,2-diaminoethane, 1,3-diaminopropane, 1,4-diaminobutane or 1,6-diaminohexane, or a mixture of two or more of these; and 3) polyimides composed of repeating unit of formula (8) in which the tetracarboxylic acid forming $R^{18}$ is 3,3',4,4'-biphenyltetracarboxylic acid, 3,3',4,4'-biphenyltetracarboxylic acid, 1,1,1,3,3,3-hexafluoro-2,2-bis(3,4-dicarboxyphenyl) propane, 1,2,3,4-cyclobutane tetracarboxylic acid, 1,2,3,4-cyclopentane tetracarboxylic acid, 1,2,4,5-cyclohexane tetracarboxylic acid, 5-succinic acid-3-methyl-3-cyclohexene-1,2-dicarboxylic acid, 3,4-dicarboxy-1,2,3,4-tetrahydronaphthalene-1-succinic acid, 1,2,3,4-butane tetracarboxylic acid or 1,2,3,4-cyclobutane tetracarboxylic acid, and the diamine forming $R^{19}$ is p-phenylenediamine, m-phenylenediamine, 3,3'-dimethyl-4,4'-diaminobiphenyl, 3,3'-diethyl-4,4'-diaminobiphenyl, 4,4'-diaminodiphenylmethane, 4,4'-diaminodiphenyl ether, bis(3,5-diethyl-4-aminophenyl)methane, 4,4'-diaminodiphenylsulfone, 1,5-diaminonaphthalene, 1,4-bis(4-aminophenoxy)benzene, 1,3-bis(4-aminophenoxy)benzene, bis(4-aminocyclohexyl)methane, bis(4-amino-3-methylcyclohexyl)methane, 1,2-diaminoethane, 1,3-diaminopropane, 1,4-diaminobutane or 1,6-diaminohexane.

The polymer compounds in the present invention are specifically limited so far as they can heterogenize an olefin oxidation catalyst prepared from a tungstic acid compound, a phosphoric acid, hydrogen peroxide and a quaternary ammonium, or an olefin oxidation catalyst prepared from a tungsten compound and a quaternary ammonium salt, and include for example polyimides, acrylamides, methacrylamides, polyamides, polyurethanes, etc. The lower limit of number average molecular weight thereof is generally $5\times10^3$, preferably $8\times10^3$, and the upper limit is $2\times10^5$, for example $1\times10^5$, or preferably for example $3\times10^4$.

Preferable polyimides include polyimides composed of repeating unit of formula (8).

The tungsten compound in the present invention includes 12-tungstophosphoric acid, sodium salt of 12-tungstophosphoric acid, potassium salt of 12-tungstophosphoric acid, ammonium salt of 12-tungstophosphoric acid, etc., and 12-tungstophosphoric acid is preferable.

In the meanwhile, the salts of 12-tungstophosphoric acid can be easily produced from 12-tungstophosphoric acid.

The tungstic acid compound in the present invention includes tungstic acid, sodium salt of tungstic acid, potassium of tungstic acid, ammonium salt of tungstic acid, and tungstic acid is preferable.

The olefin oxidation catalyst prepared from the organic compound or polymer compound of formula (1), a tungstic acid compound, phosphoric acid, hydrogen peroxide and the quaternary ammonium salt of formula (2) or (3), and the olefin oxidation catalyst prepared from the organic compound or polymer compound of formula (1), a tungsten compound and the quaternary ammonium salt of formula (2) or (3) can be prepared by modifying the process described in J. Org. Chem., Vol. 53, p. 1552-1557 (1988) and J. Org. Chem., Vol. 53, p. 3587-3593 (1988).

The olefin oxidation catalyst prepared from the organic compound or polymer compound of formula (1), a tungstic acid compound, phosphoric acid, hydrogen peroxide and the quaternary ammonium salt of formula (2) or (3) according to the present invention can be produced by adding the tungstic acid compound in an aqueous solution of hydrogen peroxide, warming and then adding phosphoric acid at room temperature, diluting with water to obtain a diluted solution, dispersing the organic compound or polymer compound of formula (1) in the diluted solution, and then adding dropwise a solution of the quaternary ammonium salt of formula (2) or (3) diluted with a solvent.

The used amount of the organic compound or polymer compound of formula (1) is 1 to 200 g per 1 mmol of phosphoric acid.

As the hydrogen peroxide used, commercially available aqueous solution can be used as such or in a diluted state, and the used amount thereof is 2 to 50 molar equivalents, preferably 2 to 30 molar equivalents based on the quaternary ammonium salt of formula (2) or (3).

The used amount of tungstic acid compound is 1 to 3 molar equivalents based on the quaternary ammonium salt of formula (2) or (3).

The used amount of phosphoric acid is 0.1 to 1 molar equivalent based on the quaternary ammonium salt of formula (2) or (3).

The solvent used is not specifically limited so long as it does not take part in the reaction, and includes aromatic hydrocarbons such as benzene, toluene, xylene and the like, aliphatic hydrocarbons such as hexane, heptane, dodecane, and the like, halogen-containing solvents, such as chloroform, dichloromethane, dichloroethane, and the like, ethers such as tetrahydrofuran, dioxane, and the like, nitriles such as acetonitrile, butyronitrile and the like, amides such as N,N-dimethylformamide, N,N-dimethylacetamide, and the like, ureas such as N,N'-dimethylimidazolidinone, and the like, water, and mixtures of these solvents. Water, aromatic hydrocarbons, aliphatic hydrocarbons, and mixtures of these solvents are preferable.

The temperature for warming is 40 to 80° C.

Next, the olefin oxidation catalyst prepared from the organic compound or polymer compound of formula (1), a tungsten compound, and the quaternary ammonium salt of formula (2) or (3) according to the present invention will be described.

The oxidation catalyst can be produced by dispersing the organic compound or polymer compound of formula (1) in a solution of the quaternary ammonium salt of formula (2) or (3) diluted with a solvent, and adding dropwise an aqueous solution of the tungsten compound therein, or by dispersing the organic compound or polymer compound of formula (1) in an aqueous solution of the tungsten compound, and adding dropwise a solution of the quaternary ammonium salt of formula (2) or (3) diluted with a solvent.

The used amount of the organic compound or polymer compound of formula (1) is 1 to 200 g per 1 mmol of the tungsten compound.

The used amount of tungsten compound is 0.2 to 0.5 molar equivalent based on the quaternary ammonium salt of formula (2) or (3).

The solvent used is not specifically limited so long as it does not take part in the reaction, and includes aromatic hydrocarbons such as benzene, toluene, xylene and the like, aliphatic hydrocarbons such as hexane, heptane, dodecane, and the like, halogen-containing solvents, such as chloroform, dichloromethane, dichloroethane, and the like, ethers such as tetrahydrofuran, dioxane, and the like, nitriles such as acetonitrile, butyronitrile and the like, amides such as N,N-dimethylformamide, N,N-dimethylacetamide, and the like, ureas such as N,N'-dimethylimidazolidinone, and the like, water, and mixtures of these solvents. Water, aromatic hydrocarbons, aliphatic hydrocarbons, and mixtures of these solvents are preferable.

In addition, the temperature in the reaction is 0 to 100° C.

The olefin oxidation catalyst according to the present invention prepared by the above-mentioned production process is generally insoluble in the solvent. Therefore, the olefin oxidation catalyst can be isolated by removing the solvent and aqueous phase after reaction.

In the meanwhile, a solution prepared by dissolving the olefin oxidation catalyst in a solvent can be used as such for the production of oxirane compounds of formula (5).

In case where the used solvent is aromatic hydrocarbons such as toluene, xylene or the like, or aliphatic hydrocarbon such as hexane, heptane, dodecane or the like, the resulting olefin oxidation catalyst is generally insoluble in the solvent, and therefore the reaction solution forms three phases composed of an aqueous phase, an organic phase and a catalyst phase.

In this case, after reaction, the removal of the aqueous and organic phases enables the olefin oxidation catalyst to be isolated.

Also in case where water is used as a solvent, the resulting olefin oxidation catalyst is generally insoluble in the solvent, and therefore the filtration or the removal of water enables the olefin oxidation catalyst to be isolated.

As to the structure of the olefin oxidation catalyst prepared from the organic compound or polymer compound of formula (1), a tungstic acid compound, phosphoric acid, hydrogen peroxide and the quaternary ammonium salt of formula (2) or (3), from the indication of J. Org. Chem., Vol. 53, p. 1553-1557 (1988), it is suggested that the compound having the following structure may be adsorbed by or dissolved in the organic compound or polymer compound of formula (1) and the resulting catalyst may be heterogenized.

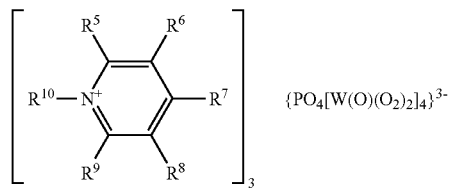

-continued

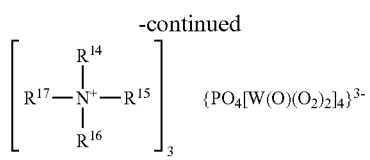

On the other hand, as to the structure of the olefin oxidation catalyst prepared from the olefin oxidation catalyst prepared from the organic compound or polymer compound of formula (1), a tungsten compound and the quaternary ammonium salt of formula (2) or (3), from the indication of J. Org. Chem., Vol. 53, p. 3587-3593 (1988), it is suggested that the compound having the following structure may be adsorbed by or dissolved in the organic compound or polymer compound of formula (1) and the resulting catalyst may be heterogenized.

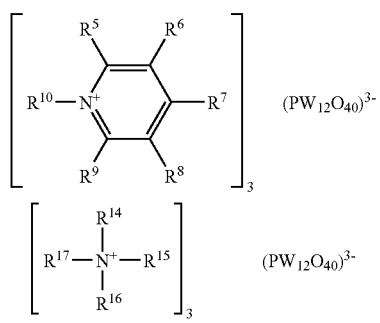

Next, the process for producing the oxirane compound of formula (5) with the olefin oxidation catalyst will be described.

According to the present invention, the oxirane compound of formula (5) can be produced by treating the olefins of formula (4) in an organic solvent with hydrogen peroxide in the presence of the olefin oxidation catalyst of the present invention.

The used amount of the olefin oxidation catalyst of the present invention is 0.03 to 15 mol % based on the olefin of formula (4) in term of the used amount of the quaternary ammonium salt used in the production of the olefin oxidation catalyst of the present invention.

The solvent used is not specifically limited so long as it does not take part in the reaction, and includes aromatic hydrocarbons such as benzene, toluene, xylene and the like, aliphatic hydrocarbons such as hexane, heptane, dodecane, and the like, ethers such as tetrahydrofuran, dioxane, and the like, nitriles such as acetonitrile, butyronitrile and the like, amides such as N,N-dimethylformamide, N,N-dimethylacetamide, and the like, ureas such as N,N'-dimethylimidazolidinone, and the like, and mixtures of these solvents. Aromatic hydrocarbons, aliphatic hydrocarbons, and mixtures of these solvents are preferable.

The reaction temperature is 0 to 150° C., but it is preferable for the synthesis of oxirane compounds that the reaction temperature is 90° C. or less.

Although pH in the reaction system is not specifically limited, it is preferably 0.5 to 7.

The control of pH in the reaction system can be carried out by adding a proper amount of phosphoric acid aqueous solution or sodium oxide aqueous solution while confirming pH with a pH meter.

The reaction can be carried out under normal pressure or pressure.

After the completion of the reaction, an organic phase containing products and the catalyst used can be easily separated by filtration process. Then, the reaction products can be purified by distillation and column chromatography to obtain an aimed product.

As the present reaction uses an aqueous solution of hydrogen peroxide (hydrogen peroxide solution), in case where any solvent insoluble in water is used, an organic phase and an aqueous phase are separated. In this case, the olefin oxidation catalyst of the present invention has generally a low solubility in organic solvents and does not have a high solubility in water. Therefore, in many cases, the reaction proceeds in a state which is separated into three phases composed of an organic phase, a catalyst phase and an aqueous phase.

As the catalyst is little dissolved in the organic phase, the solution of the oxirane compound of formula (5) can be obtained by only taking out the organic phase after the completion of the reaction.

That is, the preparation of the olefin oxidation catalyst by use of the organic compound or polymer compound of formula (1) can make the separation of the olefin oxidation catalyst easy.

In addition, the oxirane compound of formula (5) can be produced again by adding the olefin compound of formula (4) and hydrogen peroxide to the oxidation catalyst recovered with filtration after the completion of the reaction.

That is, the olefin oxidation catalyst can be re-used by using the production process of the present invention.

Further, in case where any solvent dissoluble in water is used, although the reaction is generally becomes homogeneous reaction, the separation and re-use of the olefin oxidation catalyst become possible as mentioned above by adding water and a solvent indissoluble in water to cause separation into phases.

Next, without separately preparing the olefin oxidation catalyst prepared from the organic compound or polymer compound of formula (1), a tungstic acid compound, phosphoric acid, hydrogen peroxide and the quaternary ammonium salt of formula (2) or (3), the process for producing the oxirane compound of formula (5) will be described.

The above-mentioned production process is shown in the reaction scheme described below:

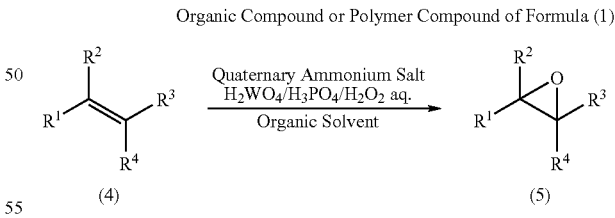

wherein $R^1$, $R^2$, $R^3$ and $R^4$ have the same meaning as the above.

That is, the oxirane compound of formula (5) can be produced by treating the olefin compound of formula (4) in an organic solvent with the organic compound or polymer compound of formula (1), tungstic acid, phosphoric acid, the quaternary ammonium salt of formula (2) or (3) and hydrogen peroxide.

The adding order of the organic compound or polymer compound of formula (1), tungstic acid, phosphoric acid, the quaternary ammonium salt of formula (2) or (3) and hydrogen peroxide used is not specifically limited.

The used amount of the organic compound or polymer compound of formula (1) is 1 to 200 g per 1 mmol of phosphoric acid.

The used amount of the quaternary ammonium salt is 0.003 to 0.15 molar equivalent based on the olefins of formula (4).

The used amount of tungstic acid is 0.004 to 0.20 molar equivalent based on the olefins of formula (4).

The used amount of phosphoric acid is 0.001 to 0.05 molar equivalent based on the olefins of formula (4).

As the hydrogen peroxide used, commercially available aqueous solution can be used as such or in a diluted state, and the used amount thereof is 0.5 to 3 molar equivalents, preferably 0.8 to 1.5 molar equivalent based on the olefins of formula (4).

In the meanwhile, as to the reaction condition, the reaction can be carried out similarly to those in the production process of oxirane compounds of formula (5) by use of the oxidation catalyst prepared from the organic compound or polymer compound of formula (1), a tungstic acid compound, phosphoric acid, hydrogen peroxide and the quaternary ammonium salt of formula (2) or (3).

In addition, the isolation and purification of the products, and the separation and re-use of the olefin oxidation catalyst can be also carried out similarly to those in the production process of oxirane compounds of formula (5) by use of the olefin oxidation catalyst according to the present invention.

The organic compounds of formula (1) used in the present invention can be produced according to known methods, for example the methods indicated in Nippon Kagaku Kaishi, Vol. 1999 (No. 2), pp. 173-178 and Bull. Soc. Chim. Fr., p. 251 (1972).

The quaternary ammonium salts of formula (2) used in the present invention can be produced according to the general synthetic method of quaternary ammonium salts as follows:

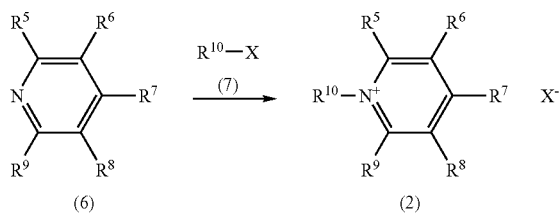

That is, the quaternary ammonium salts of formula (2) can be produced by reacting pyridines (6) with alkyl halides (7).

In addition, the salt of the quaternary ammonium salt can be exchanged by using an ion exchange resin or the like.

As the quaternary ammonium salts of formula (3) used in the present invention, commercially available ones can be used.

The polyimides composed of the repeating unit of formula (8) among the polymer compounds used in the present invention can be produced according to known methods, for example methods indicated in U.S. Pat. No. 3,489,725 and JP 6-136120 A.

As polymer compounds such as other polyimides, acrylamides, methacrylamides, polyamides, polyurethane and the like, commercially available products can be used.

EXAMPLES

Hereinafter, the present invention is further described according to examples to which the present invention is not limited.

In the meantime, as ICP emission analyzer, SPS1200A (manufactured by Seiko Instruments, Inc.) was used.

5,6-dihydrodichloropentadiene and 3,4-epoxytricyclodecane were analyzed according to the following condition:

Analyzer: GC (gas chromatography)

Analytical condition: column; HP-INNOWax (30.0 m×320 µm×0.25 µm), oven; 100° C. (maintained for 2 minutes) 20° C./min. (rise in temperature 250° C. (maintained for 5 minutes), pressure; 58.7 kPa, column flow rate; 1.4 mL/min., column average line speed; 27 cm/sec., sprit ratio; 40:1, temperature of inlet; 240° C., temperature of detector; 240° C., internal standard material; diethyl terephthalate Polyimide composed of 3,4-dicarboxy-1,2,3,4-tetrahydronaphthalene-1-succinic acid and 4,4'-diaminodiphenylmethane was produced according to Example 2 of JP 6-136120 A. In the meantime, the polyimide was analyzed according to the following condition:

Analyzer: SSC-7200 GPC SYSTEM manufactured by Senshu Scientific Co., Ltd.

Column: KD-805, KD-803 (connected in series)

Eluent: DMF

Flow rate: 1 mL/min.

Detector: RI

In addition, ethoxytricyclodecene, allyloxytricyclodecene and benzyloxytricyclodecene were produced by hydrolyzing dicyclopentenol acetate produced according to the production process described in Example 1 of JP 1-40446 A (the acetate was reacted with sodium hydroxide in water-methanol), and then etherizing (the hydrolyzed product was reacted with alkyl halide (methyl iodide, allyl chloride, benzyl bromide) in the presence of sodium hydroxide in DMF solvent).

Example 1

Preparation of Heterogeneous Catalyst with Cyanuric Acid

In a 200 mL-recovery flask equipped with a Dimroth condenser and a stirrer, 1.250 g (5.00 mmol) of tungstic acid ($H_2WO_4$) and 3.00 g (30.9 mmol) of 35% hydrogen peroxide solution was added, and stirred at 60° C. for 1 hour. After cooling the resulting white suspension to room temperature, 0.144 g (1.25 mmol) of 85% phosphoric acid ($H_3PO_4$) and 30 mL of water were added. To this solution, 5 g of cyanuric acid was added and fully dispersed, then 0.895 g (2.50 mmol) of cetyl pyridinium chloride monohydrate aqueous solution was added dropwise over 30 minutes, and stirred at room temperature overnight. The reaction solution was filtered and the resulting solid was collected. The solid was washed further with water and toluene, then dried to obtain 6.005 g of the

Example 2

Preparation of Heterogeneous Catalyst with N-Methyl Cyanuric Acid

Procedures were carried out similarly to those in Example 1, except N-methyl cyanuric acid was used instead of cyanuric acid, and 5.595 g of the entitled heterogeneous catalyst with N-methyl cyanuric acid was obtained as white solid.

ICP emission analysis: P; 0.34, W; 10.1

Example 3

Preparation of Heterogeneous Catalyst with N-Butyl Cyanuric Acid

Procedures were carried out similarly to those in Example 1, except N-butyl cyanuric acid was used instead of cyanuric acid, and 6.150 g of the entitled heterogeneous catalyst with N-butyl cyanuric acid was obtained as white solid.

ICP emission analysis: P; 0.29, W; 11.7

Example 4

Preparation of Heterogeneous Catalyst with Polyimide

Procedures were carried out similarly to those in Example 1, except polyimide composed of 3,4-dicarboxy-1,2,3,4-tetrahydronaphthalne-1-succinic acid and 4,4'-diaminodiphenylmethane was used instead of cyanuric acid, and 6.471 g of the entitled heterogeneous catalyst with polyimide was obtained as white solid. Number average molecular weight (Mn)=$1.0 \times 10^4$ ICP emission analysis: P; 0.37, W; 15.6

Example 5

Synthesis of 3,4-epoxytricyclodecane (Re-Use of Heterogeneous Catalyst with Cyanuric Acid)

In a 50 mL-four-necked flask equipped with a thermometer, a Dimroth condenser and a stirrer, 1.49 g (0.10 mmol) of heterogeneous catalyst with cyanuric acid prepared in Example 1 and 2.68 g (20.0 mmol) of 5,6-dihydrodicyclopentadiene ($C_{10}H_{14}$) and 3.49 g of toluene as a solvent were weighed out, and heated to 80° C. under stirring. Then, 2.14 g (22.0 mmol) of 35% hydrogen peroxide solution were added dropwise at the same temperature over 30 minutes, and stirred further for 1 hour. Thereafter, stirring was stopped and cooled to ordinary temperature. The reaction mixture was filtered, the catalyst filtered off was washed with toluene (100 mL). The washing and filtrate was extracted with toluene (100 mL) to obtain the entitled 3,4-epoxytricyclodecane ($C_{10}H_{14}O$) in yield 93.6% (quantitative analysis based on GC internal standard method).

(First Time Re-Use of Catalyst)

The catalyst filtered off and recovered in the above-mentioned procedures was placed again in a 50 mL-four-necked flask equipped with a thermometer, a Dimroth condenser and a stirrer, 2.68 g (20.0 mmol) of 5,6-dihydrodicyclopentadiene ($C_{10}H_{14}$) and 3.49 g of toluene were weighed out therein, and then heated to 80° C. under stirring similarly to the above. Then, 2.14 g (22.0 mmol) of 35% hydrogen peroxide solution was added dropwise at the same temperature over 30 minutes, and stirred further for 2 hours. Thereafter, stirring was stopped and cooled to ordinary temperature. The reaction mixture was filtered, the catalyst filtered off was washed with toluene (100 mL). The washing and filtrate was extracted with toluene (100 mL) to obtain the entitled 3,4-epoxytricyclodecane ($C_{10}H_{14}O$) in yield 95.9% (quantitative analysis based on GC internal standard method).

(Second Time Re-Use of Catalyst)

By using the catalyst recovered in the first time re-use, second time re-use was carried out similarly to the above (reaction time 6 hours) to obtain the entitled 3,4-epoxytricyclodecane in yield 93.3%.

(Third Time Re-Use of Catalyst)

By using the catalyst recovered in the second time re-use, third time re-use was carried out similarly to the above (reaction time 6 hours) to obtain the entitled 3,4-epoxytricyclodecane in yield 94.0%.

Example 6

Synthesis of 3,4-epoxytricyclodecane (Re-Use of Heterogeneous Catalyst with N-methyl Cyanuric Acid)

Procedures were carried out similarly to those in Example 5, except 0.909 g (0.10 mmol) of heterogeneous catalyst with N-methyl cyanuric acid prepared in Example 2 was used instead of the heterogeneous catalyst with cyanuric acid (reaction time 1 hour) to recover the catalyst and obtain the entitled 3,4-epoxytricyclodecane in yield 97.6%.

(First Time Re-Use of Catalyst)

By using the catalyst recovered in the above, first time re-use was carried out similarly to Example 5 (reaction time 1 hour) to obtain the entitled 3,4-epoxytricyclodecane in yield 95.5%.

Example 7

Synthesis of 3,4-epoxytricyclodecane (Re-Use of Heterogeneous Catalyst with N-butyl Cyanuric Acid)

Procedures were carried out similarly to those in Example 5, except 1.06 g (0.10 mmol) of heterogeneous catalyst with N-butyl cyanuric acid prepared in Example 3 was used instead of the heterogeneous catalyst with cyanuric acid (reaction time 1 hour) to recover the catalyst and obtain the entitled 3,4-epoxytricyclodecane in yield 95.8%.

(First Time Re-Use of Catalyst)

By using the catalyst recovered in the above, first time re-use was carried out similarly to Example 5 (reaction time 2 hours) to obtain the entitled 3,4-epoxytricyclodecane in yield 92.3%.

--- entitled heterogeneous catalyst with cyanuric acid as white solid.

ICP emission analysis: P; 0.18, W; 4.9

(Second Time Re-Use of Catalyst)

By using the catalyst recovered in the above, second time re-use was carried out similarly (reaction time 2 hours) to obtain the entitled 3,4-epoxytricyclodecane in yield 96.4%.

Example 8

Synthesis of 3,4-epoxytricyclodecane (Re-Use of Heterogeneous Catalyst with Polyimide)

In a 50 mL-four-necked flask equipped with a thermometer, a Dimroth condenser and a stirrer, 0.836 g (0.10 mmol) of heterogeneous catalyst with polyimide prepared in Example 4 and 2.68 g (20.0 mmol) of 5,6-dihydrodicyclopentadiene ($C_{10}H_{14}$) and 3.81 g of toluene as a solvent were weighed out, and heated to 80° C. under stirring. Then, 2.14 g (22.0 mmol) of 35% hydrogen peroxide solution was added dropwise at the same temperature over 30 minutes, and stirred further for 1 hour. Thereafter, stirring was stopped and cooled to ordinary temperature. The reaction mixture was filtered, the catalyst filtered off was washed with toluene (100 mL). The washing and filtrate was extracted with toluene (100 mL) to obtain the entitled 3,4-epoxytricyclodecane ($C_{10}H_{14}O$) in yield 99.2% (quantitative analysis based on GC internal standard method).

(First Time Re-Use of Catalyst)

The catalyst filtered off and recovered in the above-mentioned procedures was placed again in a 50 mL-four-necked flask equipped with a thermometer, a Dimroth condenser and a stirrer, 2.68 g (20.0 mmol) of 5,6-dihydrodicyclopentadiene ($C_{10}H_{14}$) and 3.81 g of toluene were weighed out therein, and then heated to 80° C. under stirring similarly to the above. Then, 2.14 g (22.0 mmol) of 35% hydrogen peroxide solution was added dropwise at the same temperature over 30 minutes, and stirred further for 30 minutes. Thereafter, stirring was stopped and cooled to ordinary temperature. The reaction mixture was filtered, the catalyst filtered off was washed with toluene (100 mL). The washing and filtrate was extracted with toluene (100 mL) to obtain the entitled 3,4-epoxytricyclodecane ($C_{10}H_{14}O$) in yield 99.8% (quantitative analysis based on GC internal standard method).

(Second Time Re-Use of Catalyst)

By using the catalyst recovered in the first time re-use, second time re-use was carried out similarly to the above (reaction time 30 minutes) to obtain the entitled 3,4-epoxytricyclodecane in yield 99.8%.

(Third Time Re-Use of Catalyst)

By using the catalyst recovered in the second time re-use, third time re-use was carried out similarly to the above (reaction time 5 hours) to obtain the entitled 3,4-epoxytricyclodecane in yield 96.0%.

(Fourth Time Re-Use of Catalyst)

By using the catalyst recovered in the third time re-use, fourth time re-use was carried out similarly to the above (reaction time 8 hours) to obtain the entitled 3,4-epoxytricyclodecane in yield 94.3%.

Example 9

Synthesis of 3,4-epoxytricyclodecane (Re-Use of Heterogeneous Catalyst with Polyimide)

In a 50 mL-four-necked flask equipped with a thermometer, a Dimroth condenser and a stirrer, 0.836 g (0.10 mmol) of heterogeneous catalyst with polyimide prepared in Example 4 and 2.68 g (20.0 mmol) of 5,6-dihydrodicyclopentadiene ($C_{10}H_{14}$) and 3.81 g of toluene as a solvent were weighed out, and heated to 80° C. under stirring. Then, 2.14 g (22.0 mmol) of 35% hydrogen peroxide solution was added dropwise at the same temperature over 30 minutes, and stirred further for 30 minutes. Thereafter, stirring was stopped and cooled to ordinary temperature. The reaction mixture was filtered, the catalyst filtered off was washed with toluene (100 mL). The washing and filtrate was extracted with toluene (100 mL) to obtain the entitled 3,4-epoxytricyclodecane ($C_{10}H_{14}O$) in yield 96.9% (quantitative analysis based on GC internal standard method).

(First Time Re-Use of Catalyst)

The catalyst filtered off and recovered in the above-mentioned procedures was placed again in a 50 mL-four-necked flask equipped with a thermometer, a Dimroth condenser and a stirrer, 2.68 g (20.0 mmol) of 5,6-dihydrodicyclopentadiene ($C_{10}H_{14}$), 20.0 mg (0.08 mmol) of tungstic acid ($H_2WO_4$), 2.35 mg (0.02 mmol) of phosphoric acid ($H_3PO_4$) and 3.81 g of toluene were weighed out therein, and then heated to 80° C. under stirring similarly to the above. Then, 2.14 g (22.0 mmol) of 35% hydrogen peroxide solution was added dropwise at the same temperature over 30 minutes, and stirred further for 30 minutes. Thereafter, stirring was stopped and cooled to ordinary temperature. The reaction mixture was filtered, the catalyst filtered off was washed with toluene (100 mL). The washing and filtrate was extracted with toluene (100 mL) to obtain the entitled 3,4-epoxytricyclodecane ($C_{10}H_{14}O$) in yield 95.9% (quantitative analysis based on GC internal standard method).

(Second Time Re-Use of Catalyst)

By using the catalyst recovered in the first time re-use, second time re-use was carried out similarly to the above (reaction time 30 minutes) to obtain the entitled 3,4-epoxytricyclodecane in yield 93.2%.

(Third Time Re-Use of Catalyst)

By using the catalyst recovered in the second time re-use, third time re-use was carried out similarly to the above (reaction time 30 minutes) to obtain the entitled 3,4-epoxytricyclodecane in yield 93.8%.

(Fourth Time Re-Use of Catalyst)

By using the catalyst recovered in the third time re-use, fourth time re-use was carried out similarly to the above (reaction time 1 hour) to obtain the entitled 3,4-epoxytricyclodecane in yield 92.1%.

(Fifth Time Re-Use of Catalyst)

By using the catalyst recovered in the fourth time re-use, fifth time re-use was carried out similarly to the above (reaction time 2 hours) to obtain the entitled 3,4-epoxytricyclodecane in yield 92.1%.

(Sixth Time Re-Use of Catalyst)

By using the catalyst recovered in the fifth time re-use, sixth time re-use was carried out similarly to the above (reaction time 2 hours) to obtain the entitled 3,4-epoxytricyclodecane in yield 93.1%.

Example 10

Synthesis of 3,4-epoxytricyclodecane (Re-Use of Heterogeneous Catalyst with Polyimide)

In a 20 L-large scaled reactor equipped with a thermometer, a Dimroth condenser and a stirrer, 298 g (29.8 mmol) of heterogeneous catalyst with polyimide prepared in Example 4 and 800 g (5.96 mmol) of 5,6-dihydrodicyclopentadiene ($C_{10}H_{14}$) and 1.04 kg of toluene as a solvent were weighed out, and heated to 60° C. under stirring. Then, 637 g (6.56 mmol) of 35% hydrogen peroxide solution were added dropwise at the same temperature over 5 hours, and stirred further for 1 hour. Thereafter, stirring was stopped and cooled to 0° C. The reaction mixture was filtered (by sucking off through glass filter), the catalyst filtered off was washed with toluene (1.49 L). From the washing and filtrate, the entitled 3,4-epoxytricyclodecane ($C_{10}H_{14}O$) was obtained.

(First Time Re-Use of Catalyst)

In the 20 L-large scaled reactor in which the catalyst filtered off and recovered in the above-mentioned procedures was placed, 800 g (5.96 mol) of 5,6-dihydrodicyclopentadiene ($C_{10}H_{14}$) and 1.04 kg of toluene were weighed out, and then heated to 60° C. under stirring similarly to the above. Then, 637 g (6.56 mol) of 35% hydrogen peroxide solution was added dropwise at the same temperature over 5.3 hours, and stirred further for 2 hours. Thereafter, stirring was stopped and cooled to ordinary temperature. The reaction mixture was filtered (by sucking off through glass filter), the catalyst filtered off was washed with toluene (1.49 L). From the washing and filtrate, the entitled 3,4-epoxytricyclodecane ($C_{10}H_{14}O$) was obtained.

(Second Time Re-Use of Catalyst)

By using the catalyst recovered in the first time re-use, second time re-use was carried out similarly to the above (reaction time 8 hours in total) to obtain the entitled 3,4-epoxytricyclodecane.

The average yield in the above-mentioned 3 batches was 93% (quantitative analysis based on GC internal standard method).

Example 11

Synthesis of ethoxy-3,4-epoxytricyclodecane

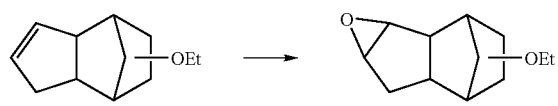

In a 50 mL-four-necked flask equipped with a thermometer, a Dimroth condenser and a stirrer, 1.29 g (0.10 mmol) of heterogeneous catalyst with cyanuric acid prepared in Example 1 and 3.57 g (20.0 mmol) of ethoxy-tricyclodecene ($C_{12}H_{18}O$) and 5.06 g of toluene as a solvent were weighed out, and heated to 80° C. under stirring. Then, 2.14 g (22.0 mmol) of 35% hydrogen peroxide solution was added dropwise at the same temperature over 30 minutes, and stirred further for 30 minutes. Thereafter, stirring was stopped and cooled with ice. The reaction mixture was filtered, the catalyst filtered off was washed with toluene (100 mL). The washing and filtrate was extracted with toluene (100 mL) to obtain the entitled ethoxy-3,4-epoxytricyclodecane ($C_{12}H_{18}O_2$) in yield 85.6% (quantitative analysis based on GC internal standard method).

Example 12

Synthesis of allyloxy 3,4-epoxytricyclodecane

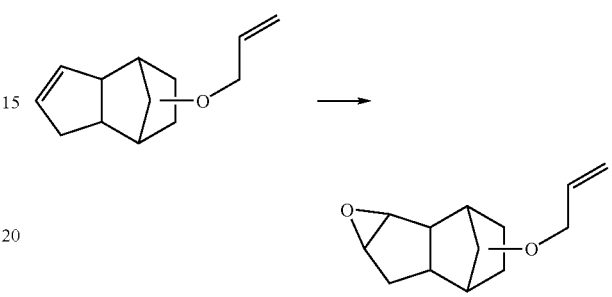

In a 50 mL-four-necked flask equipped with a thermometer, a Dimroth condenser and a stirrer, 1.29 g (0.10 mmol) of heterogeneous catalyst with cyanuric acid prepared in Example 1 and 3.81 g (20.0 mmol) of allyloxy-tricyclodecene ($C_{13}H_{18}O$) and 5.40 g of toluene as a solvent were weighed out, and heated to 40° C. under stirring. Then, 2.14 g (22.0 mmol) of 35% hydrogen peroxide solution was added dropwise at the same temperature over 30 minutes, and stirred further for 3 hours. Thereafter, stirring was stopped and cooled with ice. The reaction mixture was filtered, the catalyst filtered off was washed with toluene (100 mL). The washing and filtrate was extracted with toluene (100 mL) to obtain the entitled allyloxy 3,4-epoxytricyclodecane ($C_{13}H_{18}O_2$) in yield 66.6% (quantitative analysis based on GC internal standard method).

Example 13

Synthesis of benzyloxy 3,4-epoxytricyclodecane

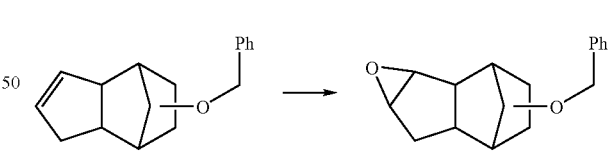

In a 50 mL-four-necked flask equipped with a thermometer, a Dimroth condenser and a stirrer, 1.29 g (0.10 mmol) of heterogeneous catalyst with cyanuric acid prepared in Example 1 and 3.57 g (20.0 mmol) of benzyloxy-tricyclodecene ($C_{17}H_{20}O$) and 6.83 g of toluene as a solvent were weighed out, and heated to 80° C. under stirring. Then, 2.14 g (22.0 mmol) of 35% hydrogen peroxide solution was added dropwise at the same temperature over 30 minutes, and stirred further for 30 minutes. Thereafter, stirring was stopped and cooled with ice. The reaction mixture was filtered, the catalyst filtered off was washed with toluene (100 mL). The washing and filtrate was extracted with toluene (100 mL) to obtain the entitled benzyloxy 3,4-epoxytricyclodecane ($C_{17}H_{20}O_2$) in yield 78.5% (quantitative analysis based on GC internal standard method).

Example 14

Synthesis of 3,4-epoxypentane nitrile

In a 50 mL-four-necked flask equipped with a thermometer, a Dimroth condenser and a stirrer, 1.29 g (0.10 mmol) of heterogeneous catalyst with cyanuric acid prepared in Example 1 and 1.71 g (20.0 mmol) of 3-pentene nitrile ($C_5H_7N$) and 2.43 g of toluene as a solvent were weighed out, and heated to 80° C. under stirring. Then, 2.14 g (22.0 mmol) of 35% hydrogen peroxide solution were added dropwise at the same temperature over 30 minutes, and stirred further for 30 minutes. Thereafter, stirring was stopped and cooled with ice. The reaction mixture was filtered, the catalyst filtered off was washed with toluene (100 mL). The washing and filtrate was extracted with toluene (100 mL) to obtain the entitled 3,4-epoxypentane nitrile ($C_5H_7NO$) in yield 44.0% (quantitative analysis based on GC internal standard method).

INDUSTRIAL APPLICABILITY

According to the process of the present invention, aimed oxirane compounds can be obtained by use of hydrogen peroxide that is economic and an clean oxidizing agent, and the catalysts used can be easily separated and re-used.

The invention claimed is:

1. A process for preparing an olefin oxidation catalyst, comprising:
adding a tungstic acid compound to a solution of hydrogen peroxide;
adding a phosphoric acid to the solution;
diluting the solution with water;
dispersing in the solution a polymer compound selected from the group consisting of polyimides, acrylamides, methacrylamides, polyamides and polyurethanes, or an organic compound of formula (1)

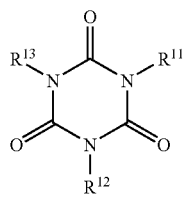

(1)

wherein $R^{11}$, $R^{12}$ and $R^{13}$ are independently of one another a hydrogen atom, a $C_{1-10}$alkyl group (the $C_{1-10}$alkyl group may be substituted by a $C_{6-10}$aryl group), a $C_{3-10}$cycloalkyl group, a $C_{6-10}$aryl group, a $C_{1-6}$alkylcarbonyl group (the $C_{1-6}$alkylcarbonyl group may be substituted by a $C_{6-10}$aryl group) or a $C_{6-10}$arylcarbonyl group; and
adding a solution of a quaternary ammonium salt of formula (2) or (3)

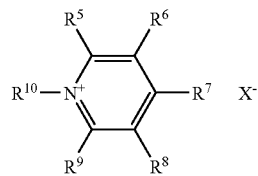

(2)

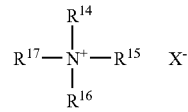

(3)

wherein $R^5$, $R^6$, $R^7$, $R^8$ and $R^9$ are independently of one another a hydrogen atom, a halogen atom, a cyano group, a $C_{1-10}$alkyl group (the $C_{1-10}$alkyl group may be substituted by a $C_{6-10}$aryl group, a $C_{1-10}$alkoxy group or a benzyloxy group), a $C_{1-10}$alkoxy group, a benzyloxy group or a phenyl group, or
any two of $R^5$, $R^6$, $R^7$, $R^8$ and $R^9$ together may form 1 or 2 fused benzene rings,
$R^{10}$, $R^{14}$, $R^{15}$, $R^{16}$ and $R^{17}$ are independently of one another a $C_{1-20}$alkyl group, and
X is a halogen atom, to the solution.

2. A process for preparing an olefin oxidation catalyst, comprising:
providing a solution of a tungsten compound, or a solution of a quaternary ammonium salt of formula (2) or (3)

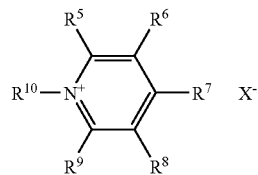

(2)

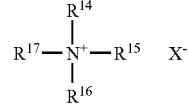

(3)

wherein $R^5$, $R^6$, $R^7$, $R^8$ and $R^9$ are independently of one another a hydrogen atom, a halogen atom, a cyano group, a $C_{1-10}$alkyl group (the $C_{1-10}$alkyl group may be arbitrarily substituted by a $C_{6-10}$aryl group, a $C_{1-10}$alkoxy group or a benzyloxy group), a $C_{1-10}$alkoxy group, a benzyloxy group or a phenyl group, or any two of $R^5$, $R^6$, $R^7$, $R^8$ and $R^9$ together may form 1 or 2 fused benzene rings,
$R^{10}$, $R^{14}$, $R^{15}$, $R^{16}$ and $R^{17}$ are independently of one another a $C_{1-20}$alkyl group, and
X is a halogen atom;
dispersing in the solution a polymer compound selected from the group consisting of polyimides, acrylamides, methacrylamides, polyamides and polyurethanes, or an organic compound of formula (1)

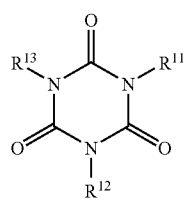

wherein $R^{11}$, $R^{12}$ and $R^{13}$ are independently of one another a hydrogen atom, a $C_{1-10}$alkyl group (the $C_{1-10}$alkyl group may be substituted by a $C_{6-10}$aryl group), a $C_{3-10}$cycloalkyl group, a $C_{6-10}$aryl group, a $C_{1-6}$alkylcarbonyl group (the $C_{1-6}$alkylcarbonyl group may be substituted by a $C_{6-10}$aryl group) or a $C_{6-10}$arylcarbonyl group; and adding the other of the solution of the tungsten compound, or the solution of the quaternary ammonium salt of formula (2) or (3) to the solution.

3. The process according to claim 1, wherein the polymer compound is composed of a repeating unit of formula (8)

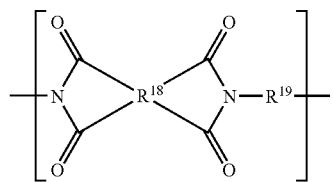

wherein $R^{18}$ is a tetravalent organic group derived from tetracarboxylic acid, and $R^{19}$ is a divalent organic group derived from diamine, and is a polyimide having a number average molecular weight of $5 \times 10^3$ or more.

4. The process according to claim 1, wherein the quaternary ammonium salt is a compound of formula (2)

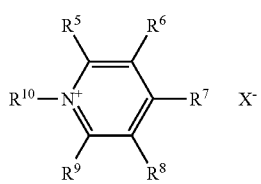

wherein $R^5$, $R^6$, $R^7$, $R^8$ and $R^9$ are independently of one another a hydrogen atom, a halogen atom, a cyano group, a $C_{1-10}$alkyl group (the $C_{1-10}$alkyl group may be substituted by a $C_{6-10}$aryl group, a $C_{1-10}$alkoxy group or a benzyloxy group), a $C_{1-10}$alkoxy group, a benzyloxy group or a phenyl group, or any two of $R^5$, $R^6$, $R^7$, $R^8$ and $R^9$ together may form 1 or 2 fused benzene rings, $R^{10}$ is a $C_{1-20}$alkyl group, and X is a halogen atom.

5. The process according to claim 4, wherein the quaternary ammonium salt of formula (2) in which $R^5$, $R^6$, $R^7$, $R^8$ and $R^9$ are hydrogen atoms is used.

6. A process for producing an oxirane compound of formula (5)

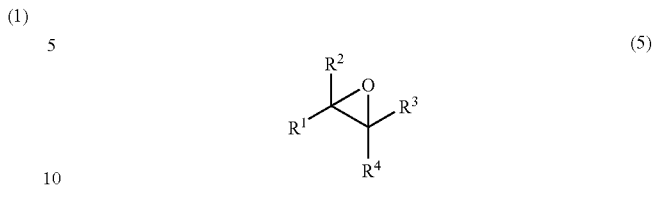

wherein $R^1$, $R^2$, $R^3$ and $R^4$ are independently of one another a hydrogen atom, a phenyl group, a $C_{1-10}$alkyl group, a $C_{3-10}$cycloalkyl group (the $C_{1-10}$alkyl group and the $C_{3-10}$cycloalkyl group may be substituted by a halogen atom, a phenyl group, a hydroxy group or a $C_{1-6}$alkoxy group), carboxyl group, a $C_{1-6}$alkylcarbonyl group, a $C_{1-6}$alkoxycarbonyl group (the $C_{1-6}$alkylcarbonyl group and the $C_{1-6}$alkoxycarbonyl group may be substituted by a halogen atom, a phenyl group, a hydroxy group or a $C_{1-6}$alkoxy group) or a phenoxycarbonyl group (the phenoxycarbonyl group may be substituted by a halogen atom, a phenyl group, a $C_{1-6}$alkyl group or a $C_{1-6}$alkoxy group), or any two of $R^1$, $R^2$, $R^3$ and $R^4$ together are —$(CH_2)_m$— wherein m is 3, 4 or 5, —$CO_2(CH_2)_n$— wherein n is 1, 2 or 3, —$CO(CH_2)_o$— wherein o is 2, 3 or 4, —$(CH_2)_p$—O—$(CH_2)_q$—wherein p and q are independently of each other 0, 1, 2, 3 or 4, and a sum of p and q is 2, 3 or 4,

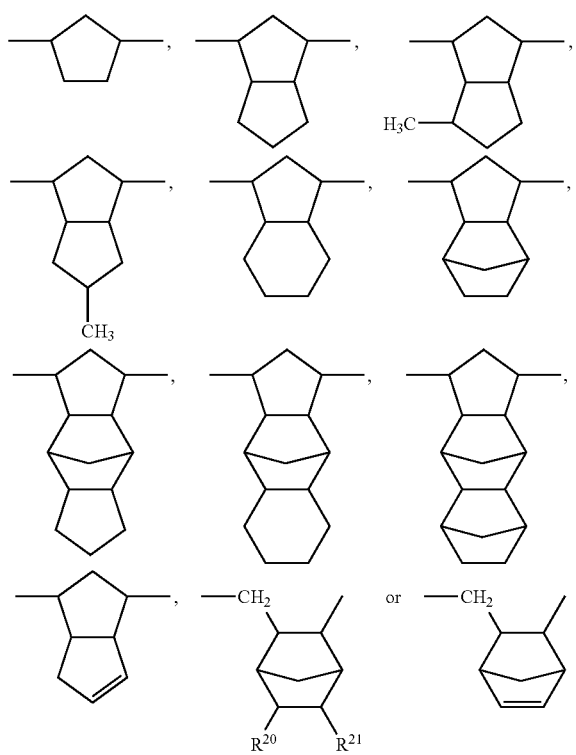

wherein $R^{20}$ and $R^{21}$ are independently of one another a hydrogen atom or a $C_{1-6}$alkoxy group (the $C_{1-6}$alkoxy group may be substituted by a $C_{2-4}$alkenyl group or a phenyl group (the phenyl group may be substituted by a halogen atom, a $C_{1-6}$alkyl group or a $C_{1-10}$alkoxy group)), comprising:

treating an olefin of formula (4)

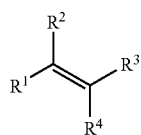
(4)

wherein $R^1$, $R^2$, $R^3$ and $R^4$ have the same meaning as the above, with hydrogen peroxide in the presence of an olefin oxidation catalyst prepared according to claim 1.

7. The process according to claim 2, wherein the polymer compound is composed of a repeating unit of formula (8)

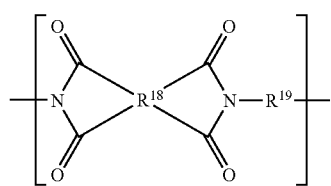
(8)

wherein $R^{18}$ is a tetravalent organic group derived from tetracarboxylic acid, and
$R^{19}$ is a divalent organic group derived from diamine, and is a polyimide having a number average molecular weight of $5 \times 10^3$ or more.

8. The process according to claim 2, wherein the quaternary ammonium salt is a compound of formula (2)

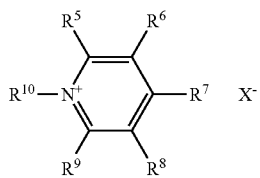
(2)

wherein $R^5$, $R^6$, $R^7$, $R^8$ and $R^9$ are independently of one another a hydrogen atom, a halogen atom, a cyano group, a $C_{1-10}$alkyl group (the $C_{1-10}$alkyl group may be substituted by a $C_{6-10}$aryl group, a $C_{1-10}$alkoxy group or a benzyloxy group), a $C_{1-10}$alkoxy group, a benzyloxy group or a phenyl group, or
any two of $R^5$, $R^6$, $R^7$, $R^8$ and $R^9$ together may form 1 or 2 fused benzene rings,
$R^{10}$ is a $C_{1-20}$alkyl group, and
X is a halogen atom.

9. The process according to claim 3, wherein the quaternary ammonium salt is a compound of formula (2)

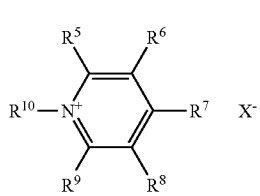
(2)

wherein $R^5$, $R^6$, $R^7$, $R^8$ and $R^9$ are independently of one another a hydrogen atom, a halogen atom, a cyano group, a $C_{1-10}$alkyl group (the $C_{1-10}$alkyl group may be substituted by a $C_{6-10}$aryl group, a $C_{1-10}$alkoxy group or a benzyloxy group), a $C_{1-10}$alkoxy group, a benzyloxy group or a phenyl group, or
any two of $R^5$, $R^6$, $R^7$, $R^8$ and $R^9$ together may form 1 or 2 fused benzene rings,
$R^{10}$ is a $C_{1-20}$alkyl group, and
X is a halogen atom.

10. A process for producing an oxirane compound of formula (5)

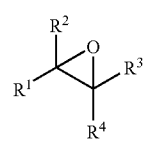
(5)

wherein $R^1$, $R^2$, $R^3$ and $R^4$ are independently of one another a hydrogen atom, a phenyl group, a $C_{1-10}$alkyl group, a $C_{3-10}$cycloalkyl group (the $C_{1-10}$alkyl group and the $C_{3-10}$cycloalkyl group may be substituted by a halogen atom, a phenyl group, a hydroxy group or a $C_{1-6}$alkoxy group), a carboxyl group, a $C_{1-6}$alkylcarbonyl group, a $C_{1-6}$alkoxycarbonyl group (the $C_{1-6}$alkylcarbonyl group and the $C_{1-6}$alkoxycarbonyl group may be substituted by a halogen atom, a phenyl group, a hydroxy group or a $C_{1-6}$alkoxy group) or a phenoxycarbonyl group (the phenoxycarbonyl group may be substituted by a halogen atom, a phenyl group, a $C_{1-6}$alkyl group or a $C_{1-6}$alkoxy group), or
any two of $R^1$, $R^2$, $R^3$ and $R^4$ together are $-(CH_2)_m-$ wherein m is 3, 4 or 5, $-CO_2(CH_2)_n-$ wherein n is 1, 2 or 3, $-CO(CH_2)_o-$ wherein o is 2, 3 or 4, $-(CH_2)_p-O-(CH_2)_q-$ wherein p and q are independently of each other 0, 1, 2, 3 or 4, and a sum of p and q is 2, 3 or 4,

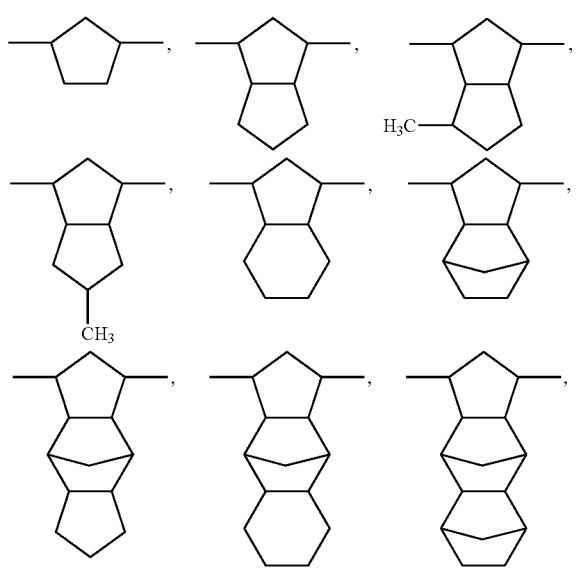

-continued

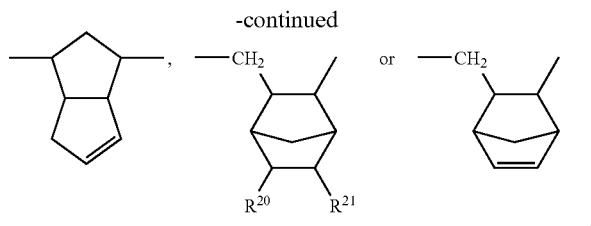

wherein $R^{20}$ and $R^{21}$ are independently of one another a hydrogen atom or a $C_{1-6}$alkoxy group (the $C_{1-6}$alkoxy group may be substituted by a $C_{2-4}$alkenyl group or a phenyl group (the phenyl group may be substituted by a halogen atom, a $C_{1-6}$alkyl group or a $C_{1-10}$alkoxy group)), comprising:
treating an olefin of formula (4)

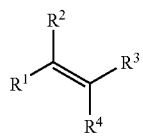
(4)

wherein $R^1$, $R^2$, $R^3$ and $R^4$ have the same meaning as the above, with hydrogen peroxide in the presence of an olefin oxidation catalyst prepared according to claim 2.

11. A process for producing an oxirane compound of formula (5)

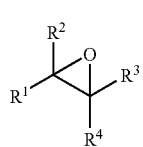
(5)

wherein $R^1$, $R^2$, $R^3$ and $R^4$ are independently of one another a hydrogen atom, a phenyl group, a $C_{1-10}$alkyl group, a $C_{3-10}$cycloalkyl group (the $C_{1-10}$alkyl group and the $C_{3-10}$cycloalkyl group may be substituted by a halogen atom, a phenyl group, a hydroxy group or a $C_{1-6}$alkoxy group), a carboxyl group, a $C_{1-6}$alkylcarbonyl group, a $C_{1-6}$alkoxycarbonyl group (the $C_{1-6}$alkylcarbonyl group and the $C_{1-6}$alkoxycarbonyl group may be substituted by a halogen atom, a phenyl group, a hydroxy group or a $C_{1-6}$alkoxy group) or a phenoxycarbonyl group (the phenoxycarbonyl group may be substituted by a halogen atom, a phenyl group, a $C_{1-6}$alkyl group or a $C_{1-6}$alkoxy group), or
any two of $R^1$, $R^2$, $R^3$ and $R^4$ together are —$(CH_2)_m$— wherein m is 3, 4 or 5, —$CO_2(CH_2)_n$— wherein n is 1, 2 or 3, —$CO(CH_2)_o$— wherein o is 2, 3 or 4, —$(CH_2)_p$—O—$(CH_2)_q$— wherein p and q are independently of each other 0, 1, 2, 3 or 4, and a sum of p and q is 2, 3 or 4,

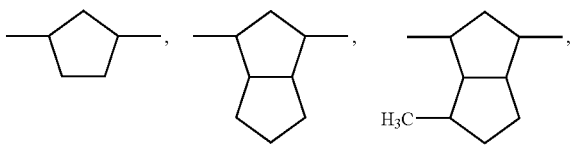

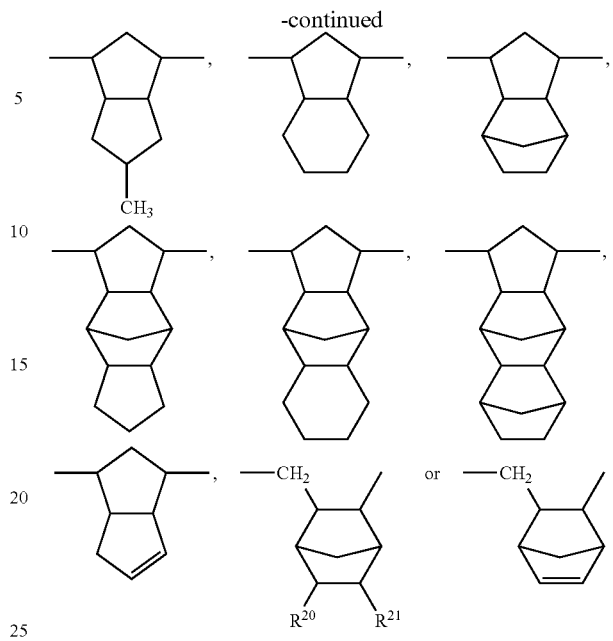

wherein $R^{20}$ and $R^{21}$ are independently of one another a hydrogen atom or a $C_{1-6}$alkoxy group (the $C_{1-6}$alkoxy group may be substituted by a $C_{2-4}$alkenyl group or a phenyl group (the phenyl group may be substituted by a halogen atom, a $C_{1-6}$alkyl group or a $C_{1-10}$alkoxy group)), comprising:
treating an olefin of formula (4)

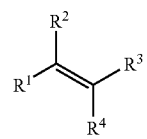
(4)

wherein $R^1$, $R^2$, $R^3$ and $R^4$ have the same meaning as the above, with hydrogen peroxide in the presence of an olefin oxidation catalyst prepared according to claim 3.

12. A process for producing an oxirane compound of formula (5)

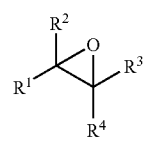
(5)

wherein $R^1$, $R^2$, $R^3$ and $R^4$ are independently of one another a hydrogen atom, a phenyl group, a $C_{1-10}$alkyl group, a $C_{3-10}$cycloalkyl group (the $C_{1-10}$alkyl group and the $C_{3-10}$cycloalkyl group may be substituted by a halogen atom, a phenyl group, a hydroxy group or a $C_{1-6}$alkoxy group), a carboxyl group, a $C_{1-6}$alkylcarbonyl group, a $C_{1-6}$alkoxycarbonyl group (the $C_{1-6}$alkylcarbonyl group and the $C_{1-6}$alkoxycarbonyl group may be substituted by a halogen atom, a phenyl group, a hydroxy group or a $C_{1-6}$alkoxy group) or a phenoxycarbonyl group (the phenoxycarbonyl group may be substituted by a halogen atom, a phenyl group, a $C_{1-6}$alkyl group or a $C_{1-6}$alkoxy group), or any two of $R^1$, $R^2$, $R^3$ and $R^4$ together are —$(CH_2)_m$— wherein m is 3, 4 or 5, —$CO_2(CH_2)_n$— wherein n is 1, 2 or 3, —$CO(CH_2)_o$— wherein o is 2, 3 or 4, —$(CH_2)_p$—O—$(CH_2)_q$— wherein p and q are independently of each other 0, 1, 2, 3 or 4, and a sum of p and q is 2, 3 or 4,

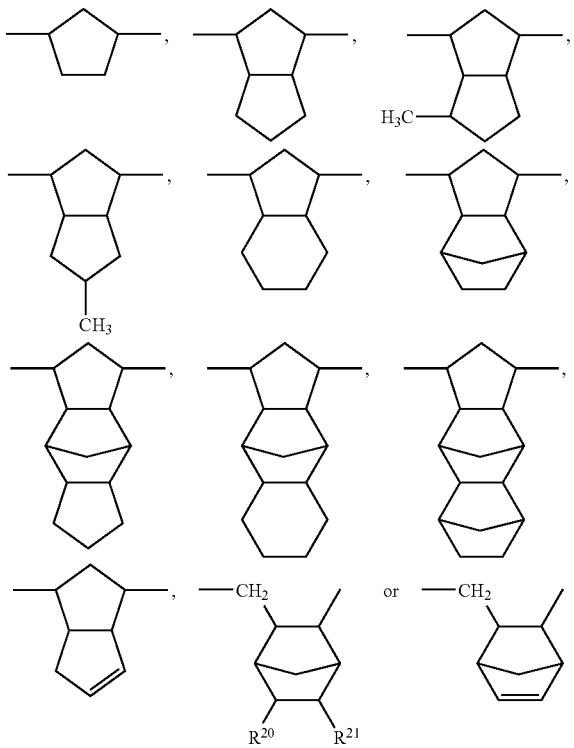

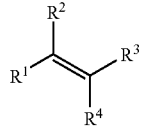 or 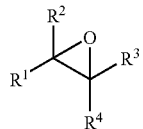

wherein $R^{20}$ and $R^{21}$ are independently of one another a hydrogen atom or a $C_{1-6}$alkoxy group (the $C_{1-6}$alkoxy group may be substituted by a $C_{2-4}$alkenyl group or a phenyl group (the phenyl group may be substituted by a halogen atom, a $C_{1-6}$alkyl group or a $C_{1-10}$alkoxy group)), comprising:

treating an olefin of formula (4)

(4)

$$R^1\phantom{xx}R^3$$
$$\phantom{xxx}C=C$$
$$R^2\phantom{xx}R^4$$

wherein $R^1$, $R^2$, $R^3$ and $R^4$ have the same meaning as the above, with hydrogen peroxide in the presence of an olefin oxidation catalyst prepared according to claim 4.

13. A process for producing an oxirane compound of formula (5)

(5)

$$R^1\phantom{xx}\overset{O}{\phantom{C}}\phantom{xx}R^3$$
$$\phantom{xxx}C—C$$
$$R^2\phantom{xx}R^4$$

wherein $R^1$, $R^2$, $R^3$ and $R^4$ are independently of one another a hydrogen atom, a phenyl group, a $C_{1-10}$alkyl group, a $C_{3-10}$cycloalkyl group (the $C_{1-10}$alkyl group and the $C_{3-10}$cycloalkyl group may be substituted by a halogen atom, a phenyl group, a hydroxy group or a $C_{1-6}$alkoxy group), a carboxyl group, a $C_{1-6}$alkylcarbonyl group, a $C_{1-6}$alkoxycarbonyl group (the $C_{1-6}$alkylcarbonyl group and the $C_{1-6}$alkoxycarbonyl group may be substituted by a halogen atom, a phenyl group, a hydroxy group or a $C_{1-6}$alkoxy group) or a phenoxycarbonyl group (the phenoxycarbonyl group may be substituted by a halogen atom, a phenyl group, a $C_{1-6}$alkyl group or a $C_{1-6}$alkoxy group), or any two of $R^1$, $R^2$, $R^3$ and $R^4$ together are —$(CH_2)_m$— wherein m is 3, 4 or 5, —$CO_2(CH_2)_n$— wherein n is 1, 2 or 3, —$CO(CH_2)_o$— wherein o is 2, 3 or 4, —$(CH_2)_p$—O—$(CH_2)_q$— wherein p and q are independently of each other 0, 1, 2, 3 or 4, and a sum of p and q is 2, 3 or 4,

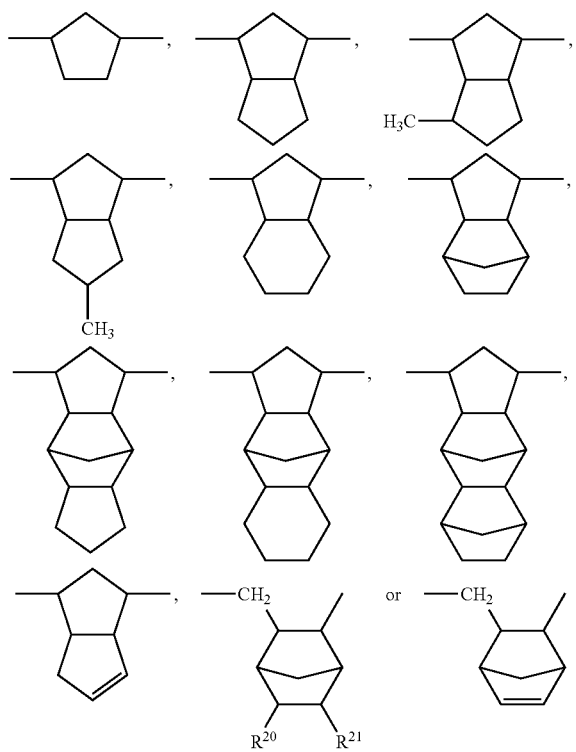

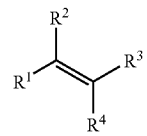 or —$CH_2$ wherein $R^{20}$ and $R^{21}$ are independently of one another a hydrogen atom or a $C_{1-6}$alkoxy group (the $C_{1-6}$alkoxy group may be substituted by a $C_{2-4}$alkenyl group or a phenyl group (the phenyl group may be substituted by a halogen atom, a $C_{1-6}$alkyl group or a $C_{1-10}$alkoxy group)), comprising:

treating an olefin of formula (4)

(4)

$$R^1\phantom{xx}R^3$$
$$\phantom{xxx}C=C$$
$$R^2\phantom{xx}R^4$$

wherein $R^1$, $R^2$, $R^3$ and $R^4$ have the same meaning as the above, with hydrogen peroxide in the presence of an olefin oxidation catalyst prepared according to claim 5.

* * * * *